(12) United States Patent  (10) Patent No.: US 7,428,200 B2
Coombs et al.  (45) Date of Patent: Sep. 23, 2008

(54) METHOD FOR TRIGGERING THROUGH DISC GROOVES AND RELATED OPTICAL ANALYSIS DISCS AND SYSTEM

(75) Inventors: James Howard Coombs, Irvine, CA (US); Kevin Robert McIntyre, Irvine, CA (US); Mark Oscar Worthington, Irvine, CA (US)

(73) Assignees: Burstein Technologies, Inc., Irvine, CA (US); Vindur Technologies, Inc., Oslo (NO)

( * ) Notice: Subject to any disclaimer, the term of this patent is extended or adjusted under 35 U.S.C. 154(b) by 0 days.

(21) Appl. No.: 11/781,104

(22) Filed: Jul. 20, 2007

(65) Prior Publication Data

US 2007/0264722 A1  Nov. 15, 2007

Related U.S. Application Data

(63) Continuation of application No. 10/351,604, filed on Jan. 23, 2003, now Pat. No. 7,251,210.

(60) Provisional application No. 60/353,724, filed on Jan. 31, 2002.

(51) Int. Cl.
*G11B 5/58* (2006.01)
*G11B 11/03* (2006.01)

(52) U.S. Cl. ............... 369/53.2; 369/53.31; 422/58; 422/68.1; 436/164; 435/287.2; 435/7.25

(58) Field of Classification Search ............. 369/53.31, 369/44.41, 53.2, 53.21, 53.22, 53.23, 53.41, 369/53.42, 275.4, 275.3, 13.54, 13.55, 47.14, 369/47.15; 422/58, 100, 101, 82.05, 68.1; 435/287.2, 39, 7.25; 436/164, 165
See application file for complete search history.

(56) References Cited

U.S. PATENT DOCUMENTS 3,555,284 A  1/1971  Anderson (Continued)

FOREIGN PATENT DOCUMENTS

EP  0 392 475 A2  10/1990

(Continued)

OTHER PUBLICATIONS

International Search Repeort for PCT/US2003/002181, filed Jan. 23, 2003.

(Continued)

*Primary Examiner*—Ali Neyzari
(74) *Attorney, Agent, or Firm*—Knobbe Martens Olson & Bear, LLP

(57) ABSTRACT

An optical analysis disc includes grooves defining corresponding laser-readable tracks and trigger marks that identify respective target regions on the disc. The trigger marks are implemented as a radial interruption of the grooves to thereby produce an increased reflection of a laser beam. There is also provided an optical analysis disc system including a trigger mechanism having a trigger detector adapted to detect interruptions in grooves of an optical analysis disc. A related method for triggering through interrupted grooves of an optical analysis disc includes detecting interruption in the grooves, generating an electrical reflection signal corresponding to the interruptions detected, and elaborating said reflection signal, so that to generate a trigger signal.

16 Claims, 23 Drawing Sheets

U.S. PATENT DOCUMENTS

| | | | |
|---|---|---|---|
| 3,736,432 | A | 5/1973 | Sweet |
| 3,798,459 | A | 3/1974 | Anderson et al. |
| 3,966,322 | A | 6/1976 | Greaves et al. |
| 4,469,793 | A | 9/1984 | Guigan |
| 4,672,600 | A | 6/1987 | Balston et al. |
| 4,677,604 | A | 6/1987 | Selby, III et al. |
| 4,687,638 | A | 8/1987 | Benajam |
| 4,748,609 | A | 5/1988 | Tsuyoshi et al. |
| 4,835,106 | A | 5/1989 | Johnson et al. |
| 4,847,205 | A | 7/1989 | Burtis et al. |
| 4,866,688 | A | 9/1989 | Tsuyoshi et al. |
| 4,870,508 | A | 9/1989 | Van Rosmalen et al. |
| 4,917,865 | A | 4/1990 | Romanauskas |
| 5,112,134 | A | 5/1992 | Chow et al. |
| 5,119,363 | A | 6/1992 | Satoh et al. |
| 5,160,702 | A | 11/1992 | Kopf-Sill et al. |
| 5,168,057 | A | 12/1992 | Oh et al. |
| 5,235,576 | A | 8/1993 | Shigemori |
| 5,281,540 | A | 1/1994 | Merkh et al. |
| 5,310,523 | A | 5/1994 | Smethers et al. |
| 5,329,461 | A | 7/1994 | Allen et al. |
| 5,407,554 | A | 4/1995 | Saurer |
| 5,424,186 | A | 6/1995 | Fodor et al. |
| 5,472,603 | A | 12/1995 | Schembri |
| 5,510,240 | A | 4/1996 | Lam et al. |
| 5,585,069 | A | 12/1996 | Zanzucchi et al. |
| 5,585,241 | A | 12/1996 | Lindmo |
| 5,593,838 | A | 1/1997 | Zanzucchi et al. |
| 5,631,844 | A | 5/1997 | Margrey et al. |
| 5,639,609 | A | 6/1997 | Kruse-Mueller et al. |
| 5,736,410 | A | 4/1998 | Zarling et al. |
| 5,859,826 | A | 1/1999 | Ueno et al. |
| 5,863,708 | A | 1/1999 | Zanzucchi et al. |
| 5,882,903 | A | 3/1999 | Andrevski et al. |
| 5,892,577 | A | 4/1999 | Gordon |
| 5,922,617 | A | 7/1999 | Wang et al. |
| 5,949,745 | A | 9/1999 | Kim |
| 5,971,941 | A | 10/1999 | Simons et al. |
| 5,982,535 | A | 11/1999 | Inoue et al. |
| 5,994,150 | A | 11/1999 | Challener et al. |
| 6,014,904 | A | 1/2000 | Lock |
| 6,017,719 | A | 1/2000 | Tseng-Law et al. |
| 6,018,713 | A | 1/2000 | Coli et al. |
| 6,030,581 | A | 2/2000 | Virtanen |
| 6,055,218 | A | 4/2000 | Takeda et al. |
| 6,100,040 | A | 8/2000 | Ramberg |
| 6,104,686 | A | 8/2000 | Whitcher et al. |
| 6,117,630 | A | 9/2000 | Reber et al. |
| 6,140,045 | A | 10/2000 | Wohlstadter et al. |
| 6,192,320 | B1 | 2/2001 | Margrey et al. |
| 6,203,992 | B1 | 3/2001 | Granados et al. |
| 6,207,369 | B1 | 3/2001 | Wohlstadter et al. |
| 6,231,812 | B1 | 5/2001 | Rothberg et al. |
| 6,241,862 | B1 | 6/2001 | McAleer et al. |
| 6,254,827 | B1 | 7/2001 | Ackley et al. |
| 6,294,326 | B1 | 9/2001 | Carrino et al. |
| 6,327,031 | B1 | 12/2001 | Gordon |
| 6,338,820 | B1 | 1/2002 | Springhorn et al. |
| 6,339,473 | B1 | 1/2002 | Gordon |
| 6,342,395 | B1 | 1/2002 | Hammock et al. |
| 6,387,331 | B1 | 5/2002 | Hunter |
| 6,451,619 | B1 | 9/2002 | Catt et al. |
| 6,476,907 | B1 | 11/2002 | Gordon |
| 6,582,662 | B1 | 6/2003 | Kellogg et al. |
| 7,026,131 | B2 | 4/2006 | Hurt et al. |
| 7,077,996 | B2 | 7/2006 | Randall et al. |
| 7,200,088 | B2 * | 4/2007 | Worthington et al. .... 369/53.31 |
| 7,221,632 | B2 * | 5/2007 | Worthington ............... 369/53.2 |
| 7,251,210 | B2 | 7/2007 | Coombs et al. |
| 2002/0076354 | A1 | 6/2002 | Cohen |
| 2002/0097658 | A1 | 7/2002 | Worthington et al. |
| 2002/0098528 | A1 | 7/2002 | Gordon et al. |
| 2002/0137059 | A1 | 9/2002 | Wu et al. |
| 2002/0137218 | A1 | 9/2002 | Mian et al. |
| 2002/0145960 | A1 | 10/2002 | Worthington et al. |
| 2002/0163642 | A1 | 11/2002 | Zoval et al. |
| 2002/0168663 | A1 | 11/2002 | Phan et al. |
| 2002/0171838 | A1 | 11/2002 | Pal et al. |
| 2002/0172980 | A1 | 11/2002 | Phan et al. |
| 2002/0176342 | A1 | 11/2002 | Worthington et al. |
| 2002/0196435 | A1 | 12/2002 | Cohen et al. |
| 2003/0003464 | A1 | 1/2003 | Phan et al. |
| 2003/0054376 | A1 | 3/2003 | Mullis et al. |
| 2003/0133840 | A1 * | 7/2003 | Coombs et al. .......... 422/82.05 |
| 2005/0037484 | A1 * | 2/2005 | Staimer et al. ........... 435/287.2 |
| 2005/0084422 | A1 * | 4/2005 | Kido et al. .................. 422/100 |
| 2008/0062839 | A1 * | 3/2008 | Worthington et al. .... 369/53.31 |

FOREIGN PATENT DOCUMENTS

| | | |
|---|---|---|
| EP | 0 521 421 A2 | 1/1993 |
| EP | 0 866 449 A2 | 9/1998 |
| GB | 2 337 113 A | 11/1999 |
| JP | 21110060 A2 | 4/2001 |
| WO | WO 96/09548 | 3/1996 |
| WO | WO 96/35940 | 11/1996 |
| WO | WO 97/18558 | 5/1997 |
| WO | WO 98/38510 | 9/1998 |
| WO | WO 00/05582 | 2/2000 |
| WO | WO 02/16037 A1 | 2/2000 |
| WO | WO 00/26677 | 5/2000 |
| WO | WO 02/06836 A2 | 1/2002 |
| WO | WO 02/42498 A2 | 5/2002 |
| WO | WO 03/036337 A2 | 5/2003 |

OTHER PUBLICATIONS

Examination Report under Article 96(2) EPC for EP Application No. 03 707 528.0, filed Jan. 23, 2006.
US 5,382,513, 01/1995, Lam et al. (withdrawn)
US 6,200,755, 03/2001, Virtanen (withdrawn)

* cited by examiner

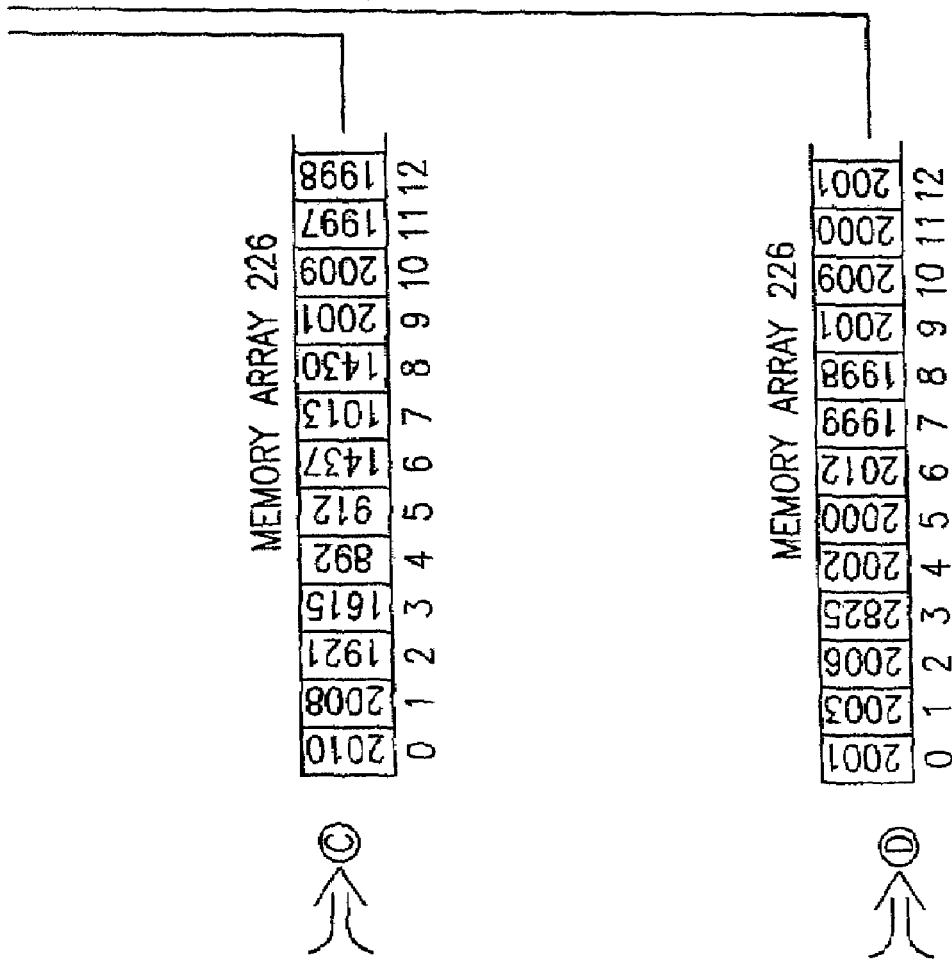

METHOD FOR TRIGGERING THROUGH DISC GROOVES AND RELATED OPTICAL ANALYSIS DISCS AND SYSTEM

CROSS-REFERENCE TO RELATED APPLICATIONS

This application is a continuation of U.S. patent application Ser. No. 10/351,604, filed Jan. 23, 2003, now U.S. Pat. No. 7,251,210 and entitled "METHOD FOR TRIGGERING THROUGH DISC GROOVES AND RELATED OPTICAL ANALYSIS DISCS AND SYSTEM" which claims the benefit of U.S. Provisional Application Ser. No. 60/353,724 filed Jan. 31, 2002 each of which is herein incorporated by reference in their entirety.

STATEMENT REGARDING COPYRIGHTED MATERIAL

Portions of the disclosure of this patent document contain material that is subject to copyright protection. The copyright owner has no objection to the facsimile reproduction by anyone of the patent document or the patent disclosure as it appears in the Patent and Trademark Office file or records, but otherwise reserves all copyright rights whatsoever.

BACKGROUND OF THE INVENTION

1. Field of the Invention

This invention relates in general to data readout from a disc and, in particular, to a correct determination of an angular position of a disc. More specifically, but without restriction to the particular embodiments hereinafter described in accordance with the best mode of practice, this invention relates to methods for triggering through interrupted grooves and related optical analysis discs and systems.

2. Discussion of the Background Art

The Optical Bio-Disc, also referred to as Bio-Compact Disc (BCD), bio-optical disc, optical analysis disc, or compact bio-disc, is now known in the art for performing various types of biochemical analyses. In particular, this optical disc utilizes the laser source of an optical storage device to detect biochemical reactions on or near the operating surface of the disc itself.

The readout of specific, localized target analysis regions on an optical reader requires that on successive rotations of the disc, either the data are captured from the same angular positions on the disc, or that the correct regions are identified after data capture.

Both require that the angular positions be recognized by the reader to sub-micron accuracy, preferably below 0.3 μm. Errors in the angular position result in misplacement of the successive lines, and therefore noise and distortions in the reconstructed image.

The discs considered have grooves that are used for generating tracking signals, the rotation of the disc resulting in the laser spot being at an increased radius of one track pitch per rotation.

In order to determine the angular position on each rotation, marks are made on the disc in either the operational layer of the disc, or on the other non-operational surfaces. Considering marks to be recognized on the operational surface, although information can be written into the grooves, these cause a reduction in reflected light intensity and can be confused with other causes of reduced light reflection, e.g. dirt etc. Therefore there is inaccuracy in determining the exact position of the mark, and error in the triggering.

SUMMARY OF THE INVENTION

The object of the present invention is to overcome limitations in the known art.

More specifically, the present invention is directed to an optical analysis disc including grooves defining corresponding laser-readable tracks on the disc and trigger marks adapted to identify respective target regions on the disc. The trigger marks are a radial interruption of the grooves adapted to produce an increased reflection of a laser beam.

Preferably, each target region of the disc is delimited by a first and a second interruptions in the corresponding grooves.

According to another embodiment of the present invention, an optical analysis disc is provided comprising grooves defining corresponding laser-readable tracks on the disc and trigger marks adapted to identify respective target regions on the disc. Each trigger mark defines a triggering region including a sequence of interruptions that produce an increased reflection of a laser beam. This defines a pattern of interrupted grooves encoding data that identifies a trigger signal. According such embodiment, the data regenerate a clock signal.

Another object of the present invention is an optical analysis disc system comprising a trigger mechanism including a trigger detector that detects interruptions in the grooves of an optical analysis disc.

According to a preferred embodiment of the system, the trigger detector is implemented to direct a laser beam toward the grooves and to detect a reflected laser beam, to thereby generate an electrical reflection signal corresponding to the reflected laser beam.

Preferably the reflection signal has a first intensity value when the laser beam is reflected by a continuous groove and a second intensity value when the laser beam is reflected by an interruption of the grooves. The second value is greater that the first.

In a specific embodiment the system according to the present invention further comprises means for elaborating the reflection signal, so as to determine a trigger signal.

Preferably the elaborating means comprises an apparatus for regenerating a clock signal, for example a slicer/PLL type apparatus.

According to another embodiment of the system, the elaborating means is adapted to perform error correction of encoded data and/or determining a clock pulse corresponding to a trigger signal, using a counter device that is implemented to count a predetermined number of clock pulses.

Another aspect of the present invention is a method for triggering through interrupted grooves of an optical analysis disc. This method includes the steps of detecting interruption in the grooves, generating an electrical reflection signal corresponding to the interruptions detected, and elaborating the reflection signal so as to generate a trigger signal.

According to a preferred embodiment of this method, the step of detecting includes directing a laser beam towards the interruption and detecting a reflected laser beam.

The reflection signal advantageously has a first intensity value when the laser beam is reflected by continuous grooves and a second intensity value when the laser beam is reflected by an interruption of the grooves, where the second value is greater than the first.

The method preferably comprises a step of regenerating a clock signal and/or a step of error correction.

According to a further embodiment of the method, the elaborating phase further comprises a step of counting a predetermined number of clock pulses for determining a pulse corresponding to a trigger signal.

This invention or different aspects thereof may be readily implemented in, adapted to, or employed in combination with the discs, assays, and systems disclosed in the following commonly assigned and co-pending patent applications: U.S. patent application Ser. No. 09/378,878 entitled "Methods and Apparatus for Analyzing Operational and Non-operational Data Acquired from Optical Discs" filed Aug. 23, 1999; U.S. Provisional Patent Application Ser. No. 60/150,288 entitled "Methods and Apparatus for Optical Disc Data Acquisition Using Physical Synchronization Markers" filed Aug. 23, 1999; U.S. patent application Ser. No. 09/421,870 entitled "Trackable Optical Discs with Concurrently Readable Analyte Material" filed Oct. 26, 1999; U.S. patent application Ser. No. 09/643,106 entitled "Methods and Apparatus for Optical Disc Data Acquisition Using Physical Synchronization Markers" filed Aug. 21, 2000; U.S. patent application Ser. No. 09/999,274 entitled "Optical Biodiscs with Reflective Layers" filed Nov. 15, 2001; U.S. patent application Ser. No. 09/988,728 entitled "Methods and Apparatus for Detecting and Quantifying Lymphocytes with Optical Biodiscs" filed Nov. 20, 2001; U.S. patent application Ser. No. 09/988,850 entitled "Methods and Apparatus for Blood Typing with Optical Bio-discs" filed Nov. 19, 2001; U.S. patent application Ser. No. 09/989,684 entitled "Apparatus and Methods for Separating Agglutinates and Disperse Particles" filed Nov. 20, 2001; U.S. patent application Ser. No. 09/997,741 entitled "Dual Bead Assays Including Optical Biodiscs and Methods Relating Thereto" filed Nov. 27, 2001; U.S. patent application Ser. No. 09/997,895 entitled "Apparatus and Methods for Separating Components of Particulate Suspension" filed Nov. 30, 2001; U.S. patent application Ser. No. 10/005,313 entitled "Optical Discs for Measuring Analytes" filed Dec. 7, 2001; U.S. patent application Ser. No. 10/006,371 entitled "Methods for Detecting Analytes Using Optical Discs and Optical Disc Readers" filed Dec. 10, 2001; U.S. patent application Ser. No. 10/006,620 entitled "Multiple Data Layer Optical Discs for Detecting Analytes" filed Dec. 10, 2001; U.S. patent application Ser. No. 10/006,619 entitled "Optical Disc Assemblies for Performing Assays" filed Dec. 10, 2001; U.S. patent application Ser. No. 10/020,140 entitled "Detection System For Disk-Based Laboratory and Improved Optical Bio-Disc Including Same" filed Dec. 14, 2001; U.S. patent application Ser. No. 10/035,836 entitled "Surface Assembly for Immobilizing DNA Capture Probes and Bead-Based Assay Including Optical Bio-Discs and Methods Relating Thereto" filed Dec. 21, 2001; U.S. patent application Ser. No. 10/038,297 entitled "Dual Bead Assays Including Covalent Linkages for Improved Specificity and Related Optical Analysis Discs" filed Jan. 4, 2002; U.S. patent application Ser. No. 10/043,688 entitled "Optical Disc Analysis System Including Related Methods for Biological and Medical Imaging" filed Jan. 10, 2002; U.S. Provisional Application Ser. No. 60/348,767 entitled "Optical Disc Analysis System Including Related Signal Processing Methods and Software" filed Jan. 14, 2002 U.S. patent application Ser. No. 10/086,941 entitled "Methods for DNA Conjugation Onto Solid Phase Including Related Optical Biodiscs and Disc Drive Systems" filed Feb. 26, 2002; U.S. patent application Ser. No. 10/087,549 entitled "Methods for Decreasing Non-Specific Binding of Beads in Dual Bead Assays Including Related Optical Biodiscs and Disc Drive Systems" filed Feb. 28, 2002; U.S. patent application Ser. No. 10/099,256 entitled "Dual Bead Assays Using Cleavable Spacers and/or Ligation to Improve Specificity and Sensitivity Including Related Methods and Apparatus" filed Mar. 14, 2002; U.S. patent application Ser. No. 10/099,266 entitled "Use of Restriction Enzymes and Other Chemical Methods to Decrease Non-Specific Binding in Dual Bead Assays and Related Bio-Discs, Methods, and System Apparatus for Detecting Medical Targets" also filed Mar. 14, 2002; U.S. patent application Ser. No. 10/121,281 entitled "Multi-Parameter Assays Including Analysis Discs and Methods Relating Thereto" filed Apr. 11, 2002; U.S. patent application Ser. No. 10/150,575 entitled "Variable Sampling Control for Rendering Pixelization of Analysis Results in a Bio-Disc Assembly and Apparatus Relating Thereto" filed May 16, 2002; U.S. patent application Ser. No. 10/150,702 entitled "Surface Assembly For Immobilizing DNA Capture Probes in Genetic Assays Using Enzymatic Reactions to Generate Signals in Optical Bio-Discs and Methods Relating Thereto" filed May 17, 2002; U.S. patent application Ser. No. 10/194,418 entitled "Optical Disc System and Related Detecting and Decoding Methods for Analysis of Microscopic Structures" filed Jul. 12, 2002; U.S. patent application Ser. No. 10/194,396 entitled "Multi-Purpose Optical Analysis Disc for Conducting Assays and Various Reporting Agents for Use Therewith" also filed Jul. 12, 2002; U.S. patent application Ser. No. 10/199,973 entitled "Transmissive Optical Disc Assemblies for Performing Physical Measurements and Methods Relating Thereto" filed Jul. 19, 2002; U.S. patent application Ser. No. 10/201,591 entitled "Optical Analysis Disc and Related Drive Assembly for Performing Interactive Centrifugation" filed Jul. 22, 2002; U.S. patent application Ser. No. 10/205,011 entitled "Method and Apparatus for Bonded Fluidic Circuit for Optical Bio-Disc" filed Jul. 24, 2002; U.S. patent application Ser. No. 10/205,005 entitled "Magnetic Assisted Detection of Magnetic Beads Using Optical Disc Drives" also filed Jul. 24, 2002; U.S. patent application Ser. No. 10/230,959 entitled "Methods for Qualitative and Quantitative Analysis of Cells and Related Optical Bio-Disc Systems" filed Aug. 29, 2002; U.S. patent application Ser. No. 10/233,322 entitled "Capture Layer Assemblies for Cellular Assays Including Related Optical Analysis Discs and Methods" filed Aug. 30, 2002; U.S. patent application Ser. No. 10/236,857 entitled "Nuclear Morphology Based Identification and Quantification of White Blood Cell Types Using Optical Bio-Disc Systems" filed Sep. 6, 2002; U.S. patent application Ser. No. 10/241,512 entitled "Methods for Differential Cell Counts Including Related Apparatus and Software for Performing Same" filed Sep. 11, 2002; U.S. patent application Ser. No. 10/279,677 entitled "Segmented Area Detector for Biodrive and Methods Relating Thereto" filed Oct. 24, 2002; U.S. patent application Ser. No. 10/293,214 entitled "Optical Bio-Discs and Fluidic Circuits for Analysis of Cells and Methods Relating Thereto" filed on Nov. 13, 2002; U.S. patent application Ser. No. 10/298,263 entitled "Methods and Apparatus for Blood Typing with Optical Bio-Discs" filed on Nov. 15, 2002; U.S. patent application Ser. No. 10/307,263 entitled "Magneto-Optical Bio-Discs and Systems Including Related Methods" filed Nov. 27, 2002; U.S. patent application Ser. No. 10/341,326 entitled "Method and Apparatus for Visualizing Data" filed Jan. 13, 2003; U.S. patent application Ser. No. 10/345,122 entitled "Methods and Apparatus for Extracting Data From an Optical Analysis Disc" filed on Jan. 14, 2003; U.S. patent application Ser. No. 10/347,155 entitled "Optical Discs Including Equi-Radial and/or Spiral Analysis Zones and Related Disc Drive Systems and Methods" filed on Jan. 15, 2003; U.S. patent application Ser. No. 10/347,119 entitled "Bio-Safe Dispenser and Optical Analysis Disc Assembly" filed Jan. 17, 2003; and U.S. patent application Ser. No. 10/353,777 entitled "Processes for Manufacturing Optical Analysis Discs with Molded Microfluidic Structures and Discs Made According Thereto" filed on Jan. 27, 2003. All of these applications are herein incorporated by reference in their entireties. They thus provide background and related disclosure as support hereof as if fully repeated herein.

The above described methods and apparatus according to the present invention as disclosed herein can have one or more advantages which include, but are not limited to, simple and quick on-disc processing without the necessity of an experienced technician to run the test, small sample volumes, use of inexpensive materials, and use of known optical disc formats and drive manufacturing. These and other features and advantages will be better understood by reference to the following detailed description when taken in conjunction with the accompanying drawing figures and technical examples.

BRIEF DESCRIPTION OF THE DRAWINGS

Further objects of the present invention together with additional features contributing thereto and advantages accruing therefrom will be apparent from the following description of the preferred embodiments of the invention which are shown in the accompanying drawing figures with like reference numerals indicating like components throughout, wherein:

FIG. 20 is a graphical representation illustrating the relationship between FIGS. 20A, 20B, 20C, and 20D;

FIGS. 20A, 20B, 20C, and 20D, when taken together, form a pictorial graphical representation of transformation of the signature traces from FIG. 19B into digital signals that are stored as one-dimensional arrays and combined into a two-dimensional array for data input;

DETAILED DESCRIPTION OF THE INVENTION

The present invention is directed to disc drive systems, optical bio-discs, image processing techniques, analysis methods, and related software. Each of these aspects of the present invention is discussed below in further detail.

Drive System and Related Discs

Figure 1:
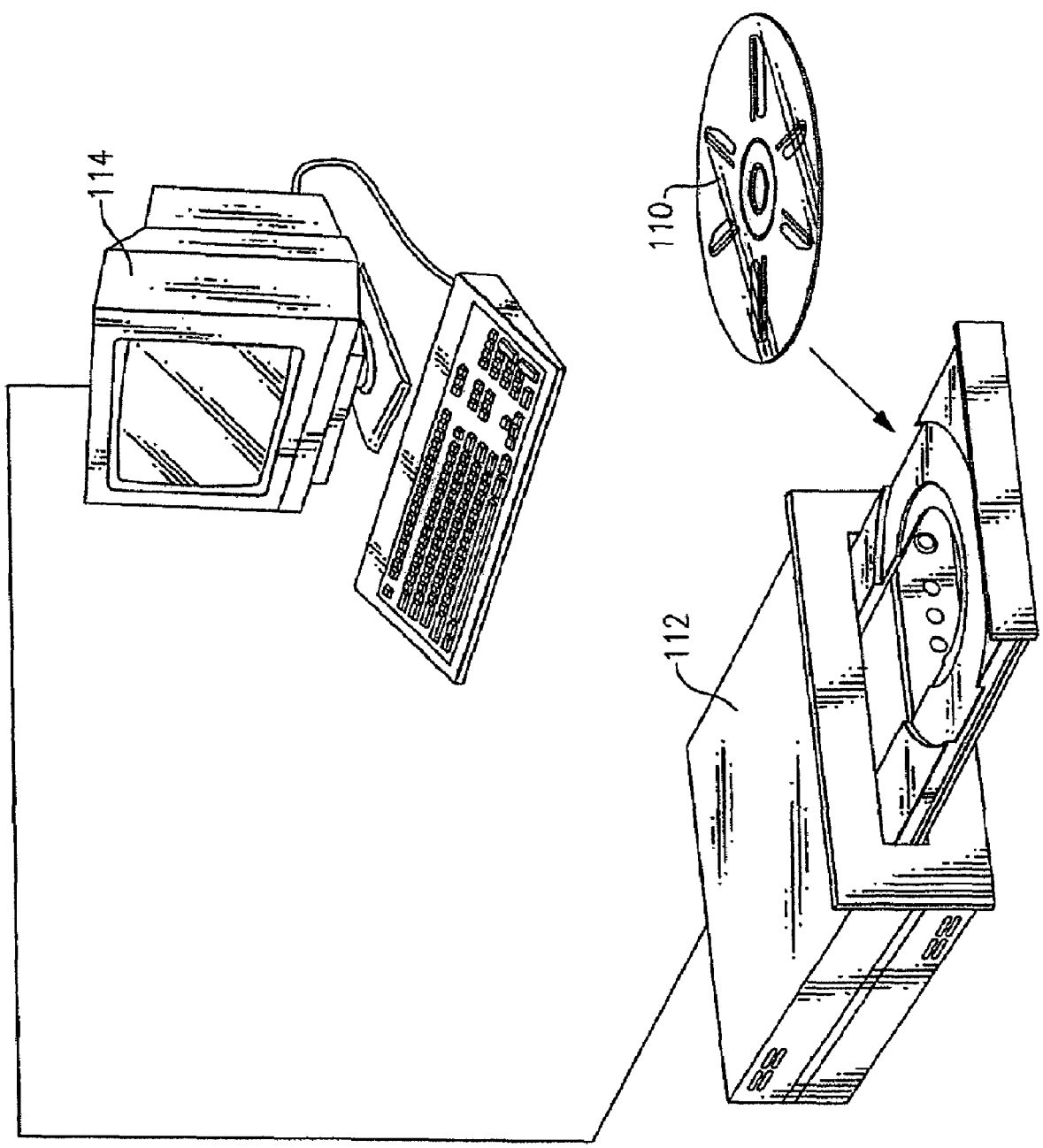
FIG. 1 is a pictorial representation of a bio-disc system.

FIG. 1 is a perspective view of an optical bio-disc 110 for conducting biochemical analyses, and in particular cell counts and differential cell counts. The present optical bio-disc 110 is shown in conjunction with an optical disc drive 112 and a display monitor 114. Further details relating to this type of disc drive and disc analysis system are disclosed in commonly assigned and co-pending U.S. patent application Ser. No. 10/008,156 entitled "Disc Drive System and Methods for Use with Bio-discs" filed Nov. 9, 2001 and U.S. patent application Ser. No. 10/043,688 entitled "Optical Disc Analysis System Including Related Methods For Biological and Medical Imaging" filed Jan. 10, 2002, both of which are herein incorporated by reference.

Figure 2:
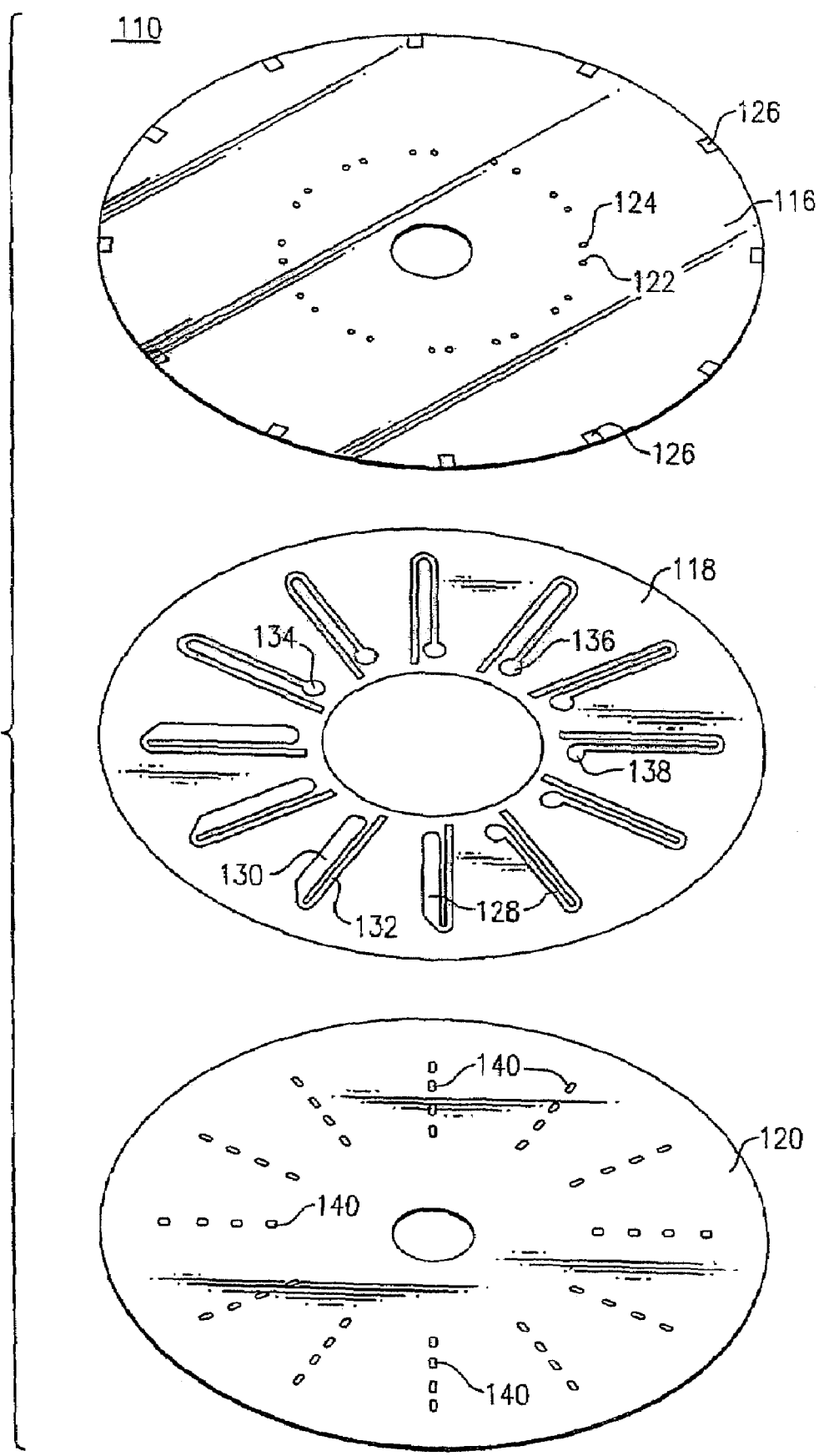
FIG. 2 is an exploded perspective view of a reflective bio-disc.
Figure 6:
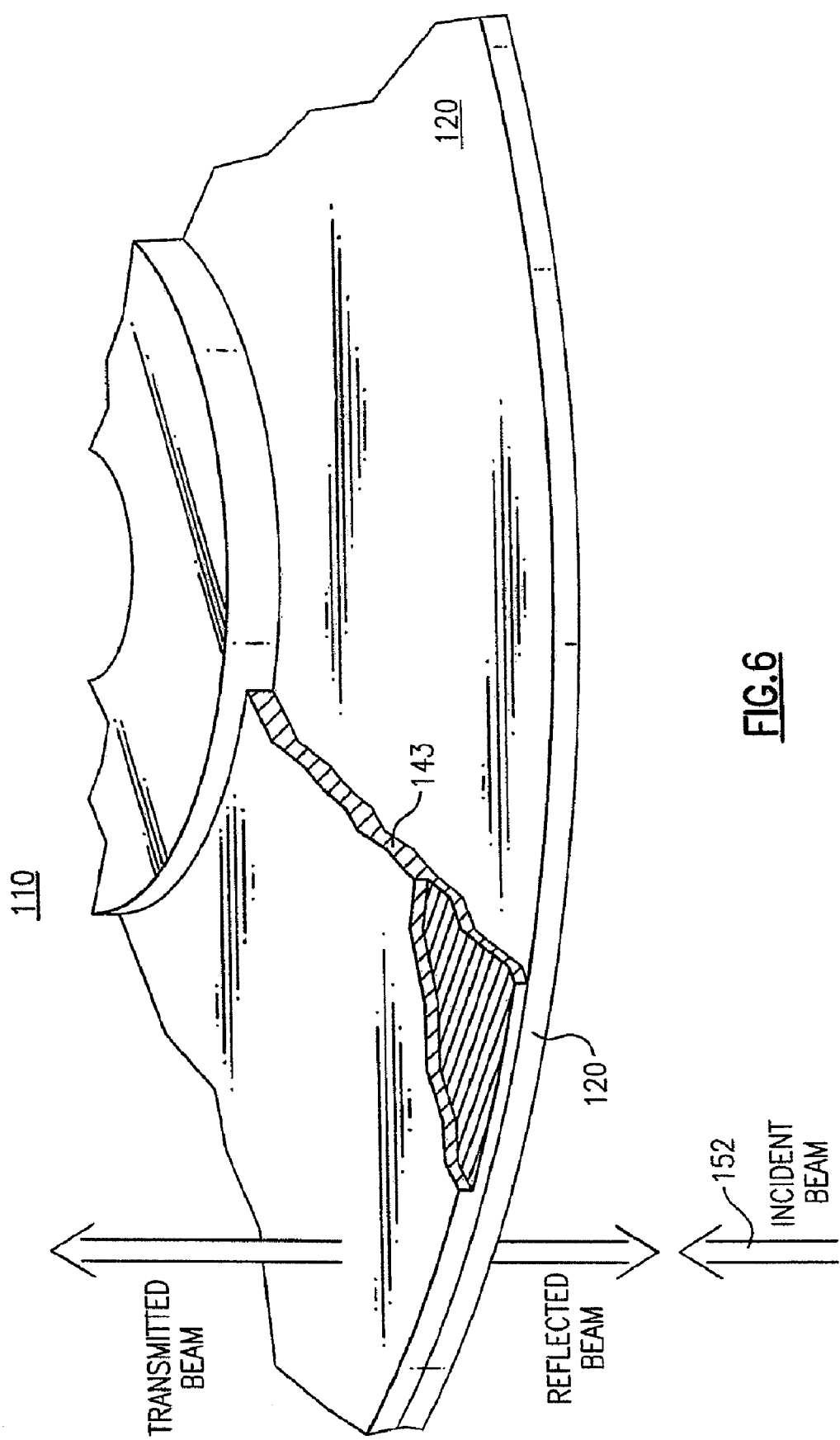
FIG. 6 is a perspective view representing the disc shown in FIG. 5 with a cut-away section illustrating the functional aspects of a semi-reflective layer of the disc.
Figure 10:
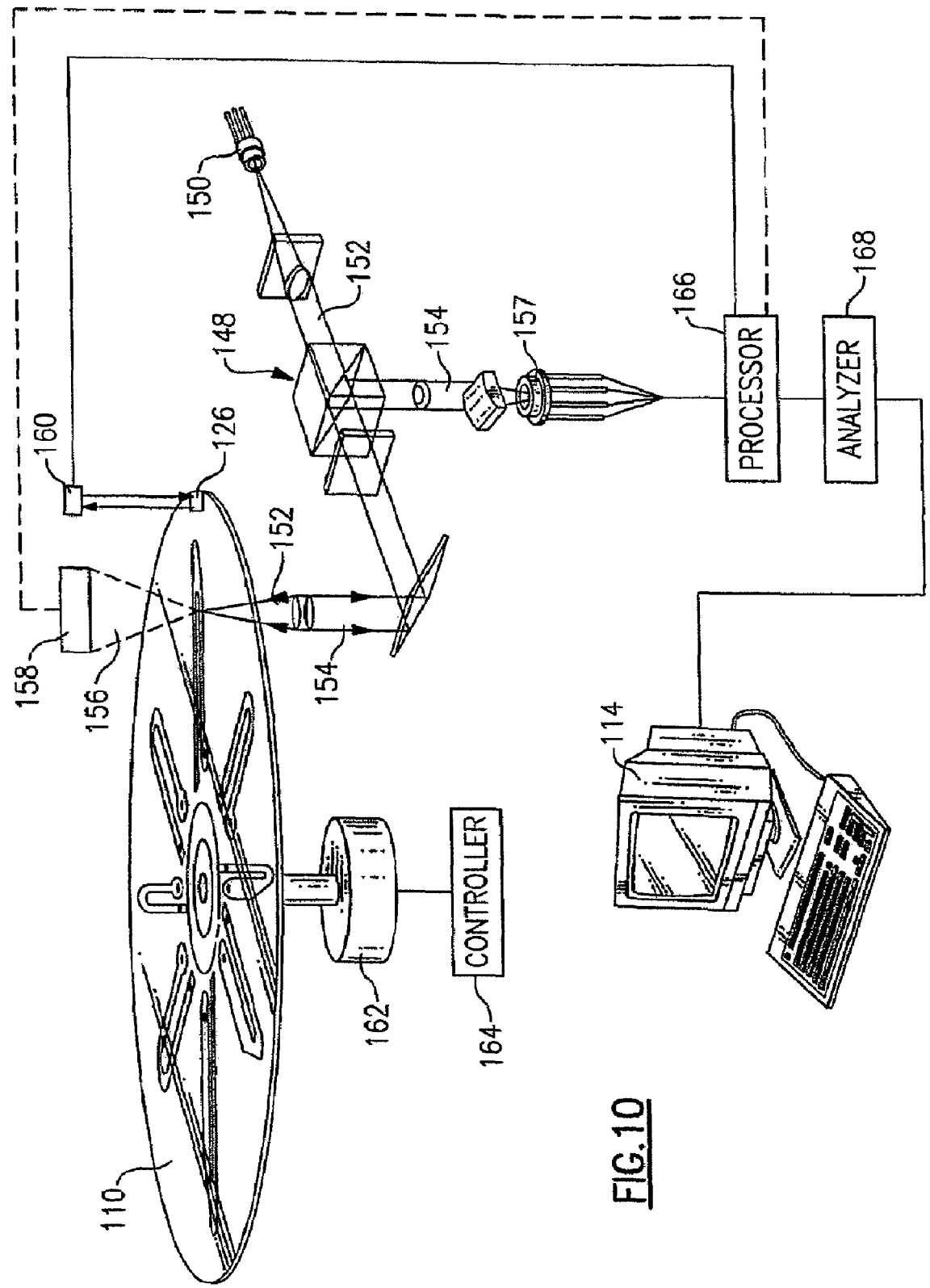
FIG. 10 is a perspective and block diagram representation illustrating the system of FIG. 1 in more detail.

FIG. 2 is an exploded perspective view of the principal structural elements of one embodiment of the optical bio-disc 110. FIG. 2 is an example of a reflective zone optical bio-disc 110 (hereinafter "reflective disc") that may be used in the present invention. The principal structural elements include a cap portion 116, an adhesive member or channel layer 118, and a substrate 120. The cap portion 116 includes one or more inlet ports 122 and one or more vent ports 124. The cap portion 116 may be formed from polycarbonate and is preferably coated with a reflective surface 146 (shown in FIG. 4) on the bottom thereof as viewed from the perspective of FIG. 2. In the preferred embodiment, trigger marks or markings 126 are included on the surface of a reflective layer 142 (shown FIG. 4). Trigger markings 126 may include a clear window in all three layers of the bio-disc, an opaque area, or a reflective or semi-reflective area encoded with information that sends data to a processor 166, as shown FIG. 10, that in turn interacts with the operative functions of an interrogation or incident beam 152, as shown in FIGS. 6 and 10.

The second element shown in FIG. 2 is an adhesive member or channel layer 118 having fluidic circuits 128 or U-channels formed therein. The fluidic circuits 128 are formed by stamping or cutting the membrane to remove plastic film and form the shapes as indicated. Each of the fluidic circuits 128 includes a flow channel 130 and a return channel 132. Some of the fluidic circuits 128 illustrated in FIG. 2 include a mixing chamber 134. Two different types of mixing chambers 134 are illustrated. The first is a symmetric mixing chamber 136 that is symmetrically formed relative to the flow channel 130. The second is an off-set mixing chamber 138. The off-set mixing chamber 138 is formed to one side of the flow channel 130 as indicated.

The third element illustrated in FIG. 2 is a substrate 120 including target or capture zones 140. The substrate 120 is preferably made of polycarbonate and has the aforementioned reflective layer 142 deposited on the top thereof (shown in FIG. 4). The target zones 140 are formed by removing the reflective layer 142 in the indicated shape or alternatively in any desired shape. Alternatively, the target zone 140 may be formed by a masking technique that includes masking the target zone 140 area before applying the reflective layer 142. The reflective layer 142 may be formed from a metal such as aluminum or gold.

Figure 3:
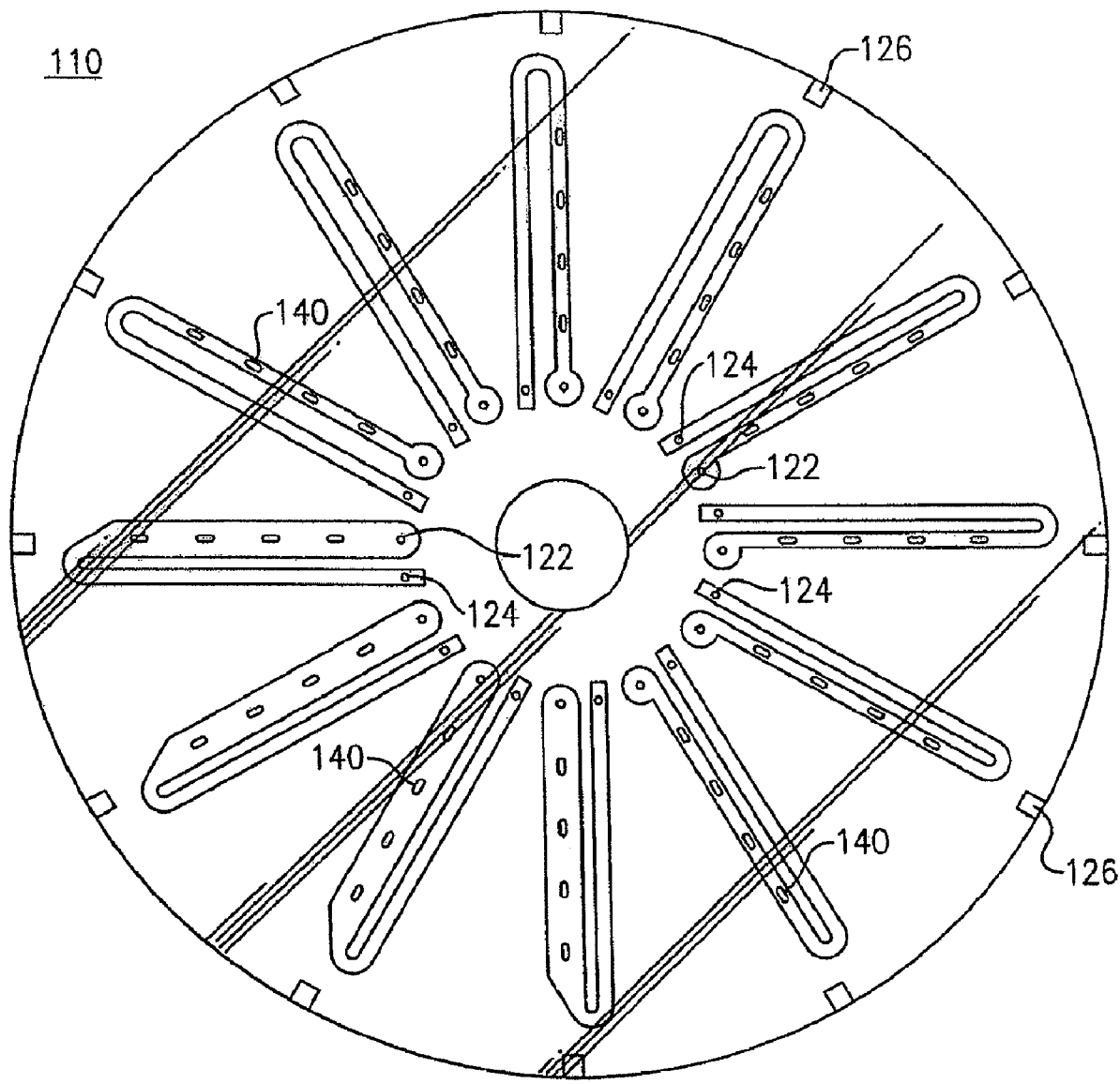
FIG. 3 is a top plan view of the disc shown in FIG. 2.

FIG. 3 is a top plan view of the optical bio-disc 110 illustrated in FIG. 2 with the reflective layer 146 on the cap portion 116 shown as transparent to reveal the fluidic circuits 128, the target zones 140, and trigger markings 126 situated within the disc.

Figure 4:
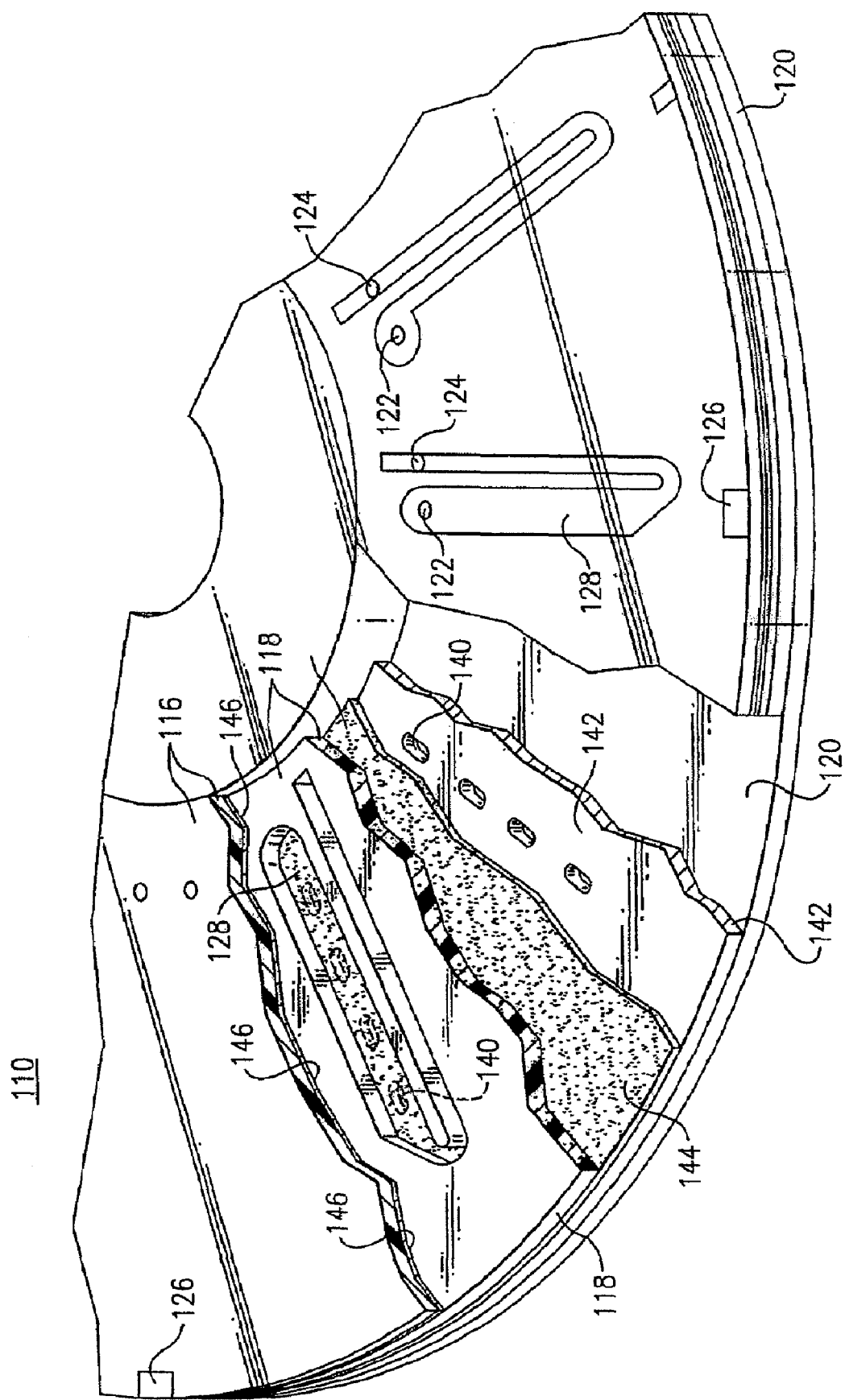
FIG. 4 is a perspective view of the disc illustrated in FIG. 2 with cut-away sections showing the different layers of the disc.

FIG. 4 is an enlarged perspective view of the reflective zone type optical bio-disc 110 according to one embodiment that may be used in the present invention. This view includes a portion of the various layers thereof, cut away to illustrate a partial sectional view of each principal layer, substrate, coating, or membrane. FIG. 4 shows the substrate 120 that is coated with the reflective layer 142. An active layer 144 is applied over the reflective layer 142. In the preferred embodiment, the active layer 144 may be formed from polystyrene. Alternatively, polycarbonate, gold, activated glass, modified glass, or modified polystyrene, for example, polystyrene-co-maleic anhydride, may be used. In addition, hydrogels can be used. Alternatively, as illustrated in this embodiment, the plastic adhesive member 118 is applied over the active layer 144. The exposed section of the plastic adhesive member 118 illustrates the cut out or stamped U-shaped form that creates the fluidic circuits 128. The final principal structural layer in this reflective zone embodiment of the present bio-disc is the cap portion 116. The cap portion 116 includes the reflective surface 146 on the bottom thereof. The reflective surface 146 may be made from a metal such as aluminum or gold.

Figure 5:
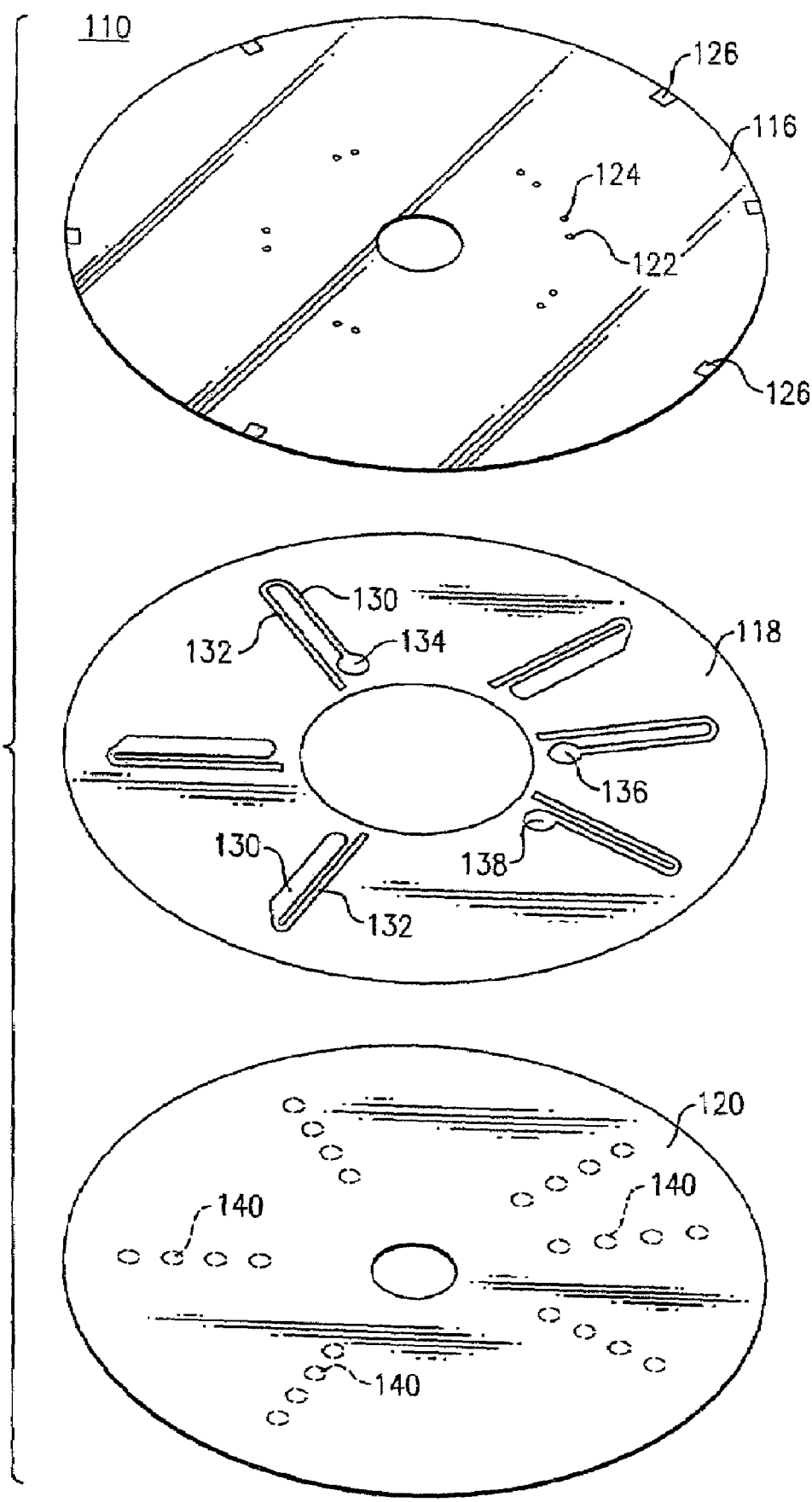
FIG. 5 is an exploded perspective view of a transmissive bio-disc.
Figure 9:
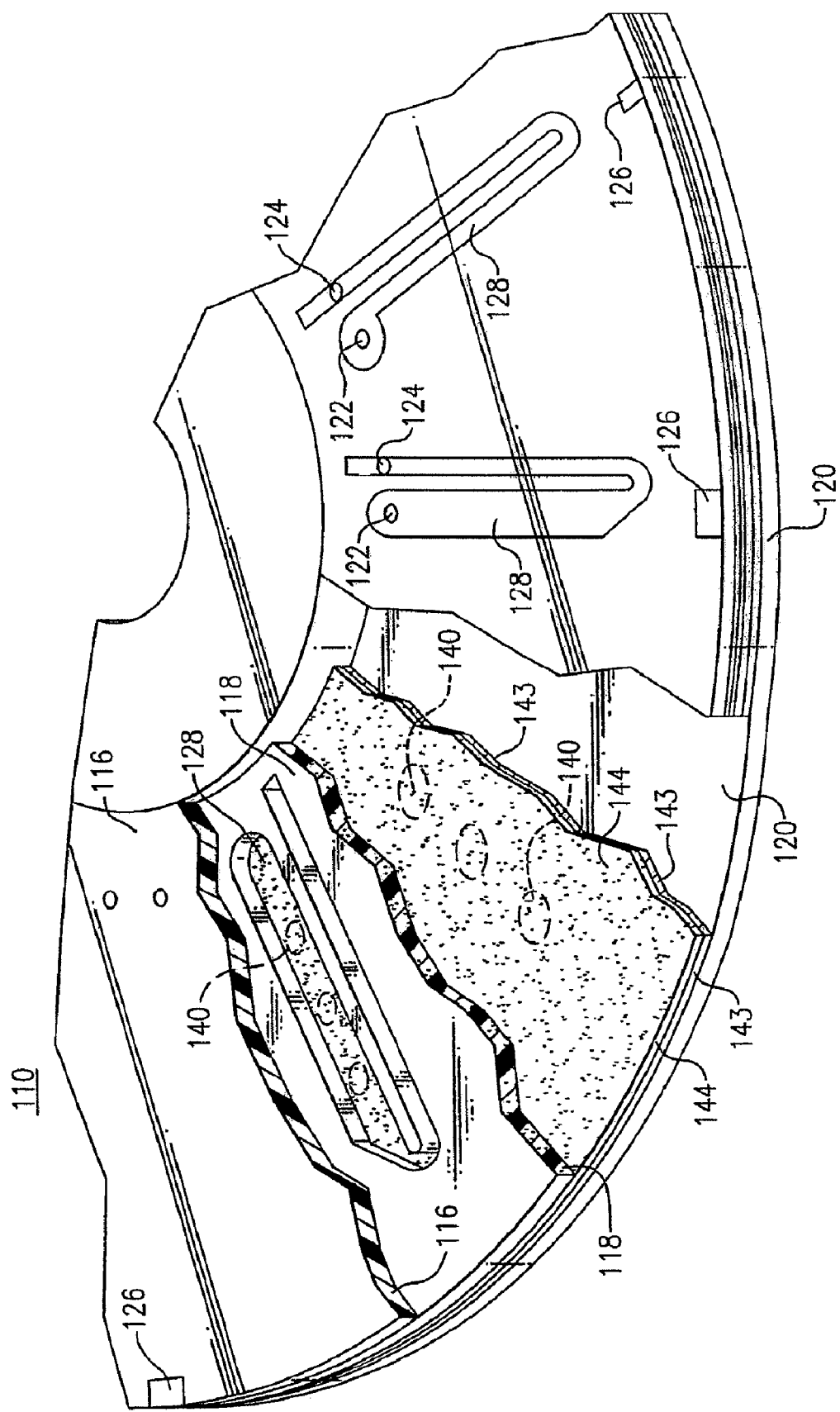
FIG. 9 is a perspective view of the disc illustrated in FIG. 5 with cut-away sections showing the different layers of the disc including the type of semi-reflective layer shown in FIG. 6.

Referring now to FIG. 5, there is shown an exploded perspective view of the principal structural elements of a transmissive type of optical bio-disc 110. The principal structural elements of the transmissive type of optical bio-disc 110 similarly include the cap portion 116, the adhesive or channel member 118, and the substrate 120 layer. The cap portion 116 includes one or more inlet ports 122 and one or more vent ports 124. The cap portion 116 may be formed from a polycarbonate layer. Optional trigger markings 126 may be included on the surface of a thin semi-reflective layer 143, as best illustrated in FIGS. 6 and 9. Trigger markings 126 may include a clear window in all three layers of the bio-disc, an opaque area, or a reflective or semi-reflective area encoded with information that sends data to a processor 166, FIG. 10, which in turn interacts with the operative functions of an interrogation beam 152, FIGS. 6 and 10.

The second element shown in FIG. 5 is the adhesive member or channel layer 118 having fluidic circuits 128 or U-channels formed therein. The fluidic circuits 128 are formed by stamping or cutting the membrane to remove plastic film and form the shapes as indicated. Each of the fluidic circuits 128 includes the flow channel 130 and the return channel 132. Some of the fluidic circuits 128 illustrated in FIG. 5 include a mixing chamber 134. Two different types of mixing chambers 134 are illustrated. The first is a symmetric mixing chamber 136 that is symmetrically formed relative to the flow channel 130. The second is an off-set mixing chamber 138. The off-set mixing chamber 138 is formed to one side of the flow channel 130 as indicated.

Figure 12:
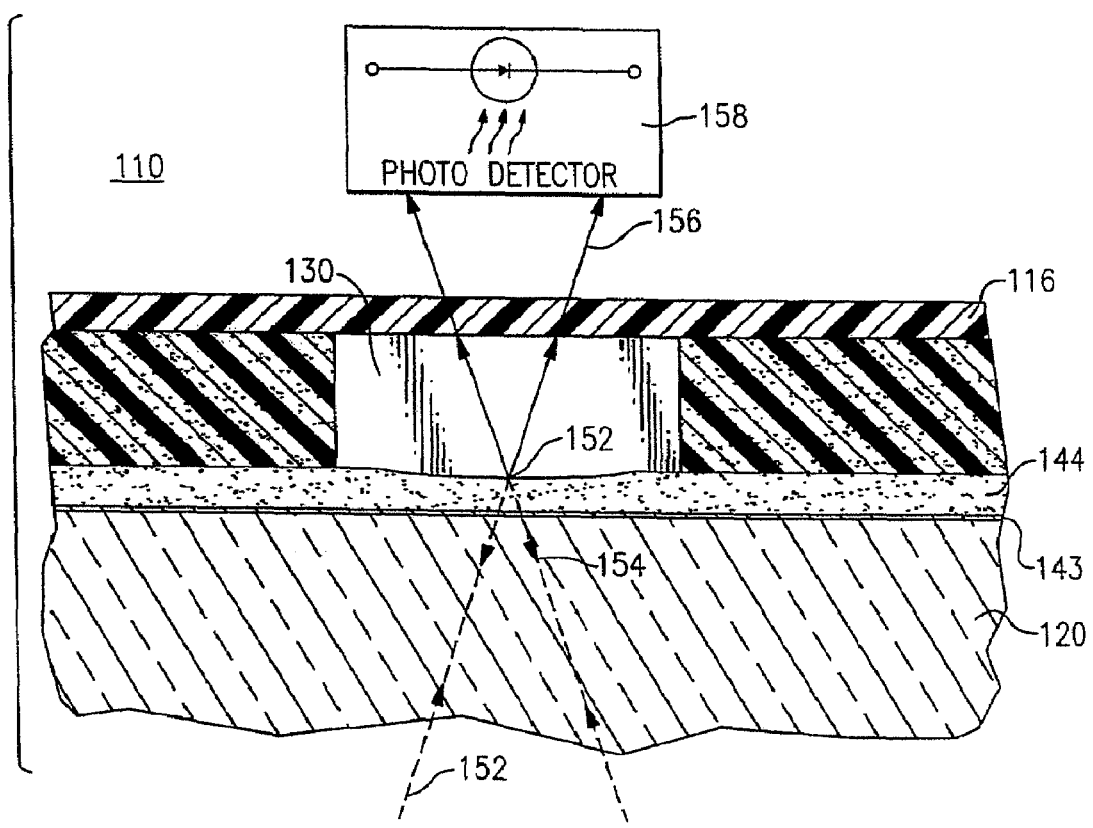
FIG. 12 is a partial cross sectional view taken perpendicular to a radius of the transmissive optical bio-disc illustrated in FIGS. 5, 8, and 9 showing a flow channel formed therein and a top detector.

The third element illustrated in FIG. 5 is the substrate 120 which may include target or capture zones 140. The substrate 120 is preferably made of polycarbonate and has the aforementioned thin semi-reflective layer 143 deposited on the top thereof, FIG. 6. The semi-reflective layer 143 associated with the substrate 120 of the disc 110 illustrated in FIGS. 5 and 6 is significantly thinner than the reflective layer 142 on the substrate 120 of the reflective disc 110 illustrated in FIGS. 2, 3 and 4. The thinner semi-reflective layer 143 allows for some transmission of the interrogation beam 152 through the structural layers of the transmissive disc as shown in FIGS. 6 and 12. The thin semi-reflective layer 143 may be formed from a metal such as aluminum or gold.

FIG. 6 is an enlarged perspective view of the substrate 120 and semi-reflective layer 143 of the transmissive embodiment of the optical bio-disc 110 illustrated in FIG. 5. The thin semi-reflective layer 143 may be made from a metal such as aluminum or gold. In the preferred embodiment, the thin semi-reflective layer 143 of the transmissive disc illustrated in FIGS. 5 and 6 is approximately 100-300 Å thick and does not exceed 400 Å. This thinner semi-reflective layer 143 allows a portion of the incident or interrogation beam 152 to penetrate and pass through the semi-reflective layer 143 to be detected by a top detector 158, FIGS. 10 and 12, while some of the light is reflected or returned back along the incident path. As indicated below, Table 1 presents the reflective and transmissive characteristics of a gold film relative to the thickness of the film. The gold film layer is fully reflective at a thickness greater than 800 Å. While the threshold density for transmission of light through the gold film is approximately 400 Å.

Figure 7:
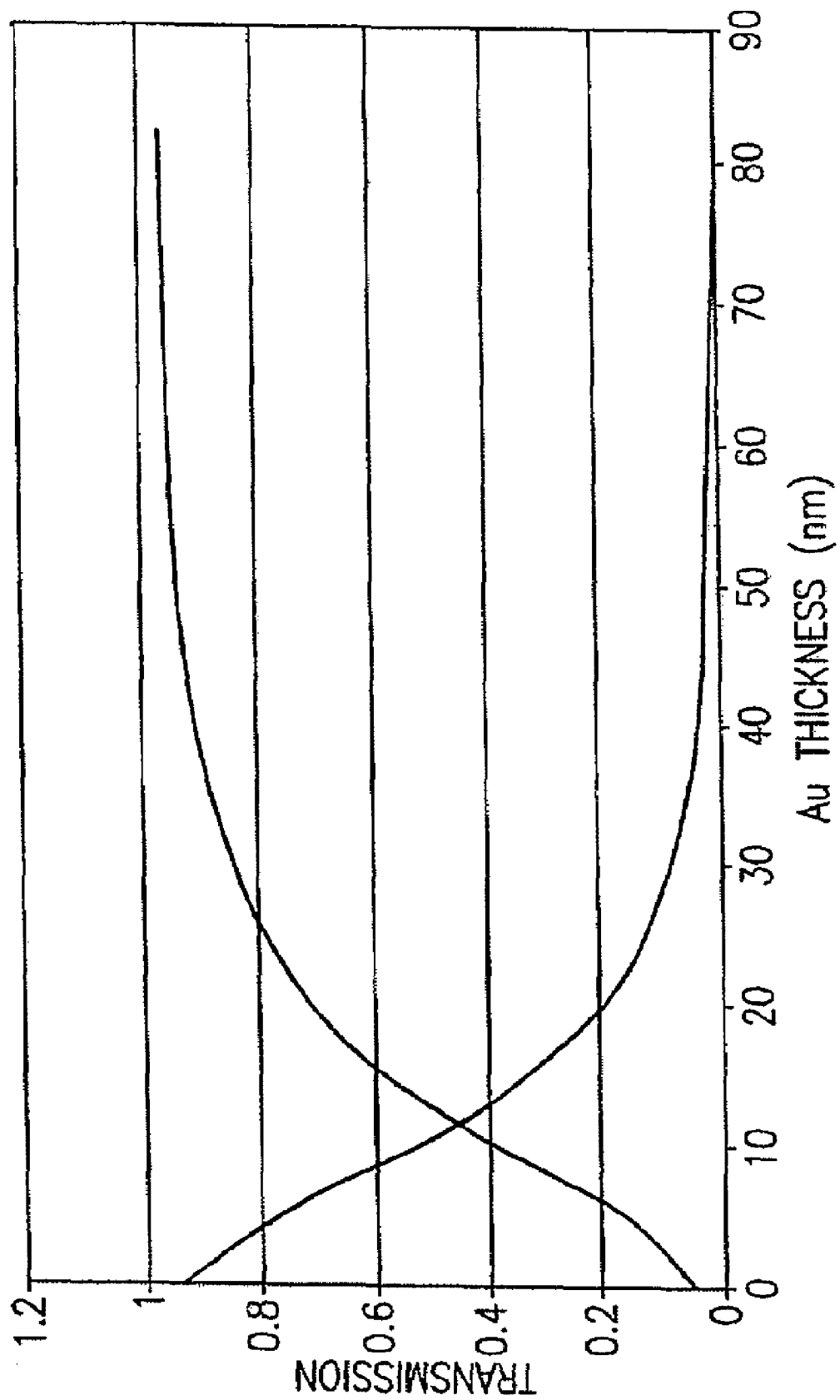
FIG. 7 is a graphical representation showing the relationship between thickness and transmission of a thin gold film.

In addition to Table 1, FIG. 7 provides a graphical representation of the inverse relationship of the reflective and transmissive nature of the thin semi-reflective layer 143 based upon the thickness of the gold. Reflective and transmissive values used in the graph illustrated in FIG. 7 are absolute values.

TABLE 1

| Au film Reflection and Transmission (Absolute Values) | | | |
|---|---|---|---|
| Thickness (Angstroms) | Thickness (nm) | Reflectance | Transmittance |
| 0 | 0 | 0.0505 | 0.9495 |
| 50 | 5 | 0.1683 | 0.7709 |
| 100 | 10 | 0.3981 | 0.5169 |
| 150 | 15 | 0.5873 | 0.3264 |
| 200 | 20 | 0.7142 | 0.2057 |
| 250 | 25 | 0.7959 | 0.1314 |
| 300 | 30 | 0.8488 | 0.0851 |
| 350 | 35 | 0.8836 | 0.0557 |
| 400 | 40 | 0.9067 | 0.0368 |

TABLE 1-continued

Au film Reflection and Transmission (Absolute Values)

| Thickness (Angstroms) | Thickness (nm) | Reflectance | Transmittance |
|---|---|---|---|
| 450 | 45 | 0.9222 | 0.0244 |
| 500 | 50 | 0.9328 | 0.0163 |
| 550 | 55 | 0.9399 | 0.0109 |
| 600 | 60 | 0.9448 | 0.0073 |
| 650 | 65 | 0.9482 | 0.0049 |
| 700 | 70 | 0.9505 | 0.0033 |
| 750 | 75 | 0.9520 | 0.0022 |
| 800 | 80 | 0.9531 | 0.0015 |

Figure 8:
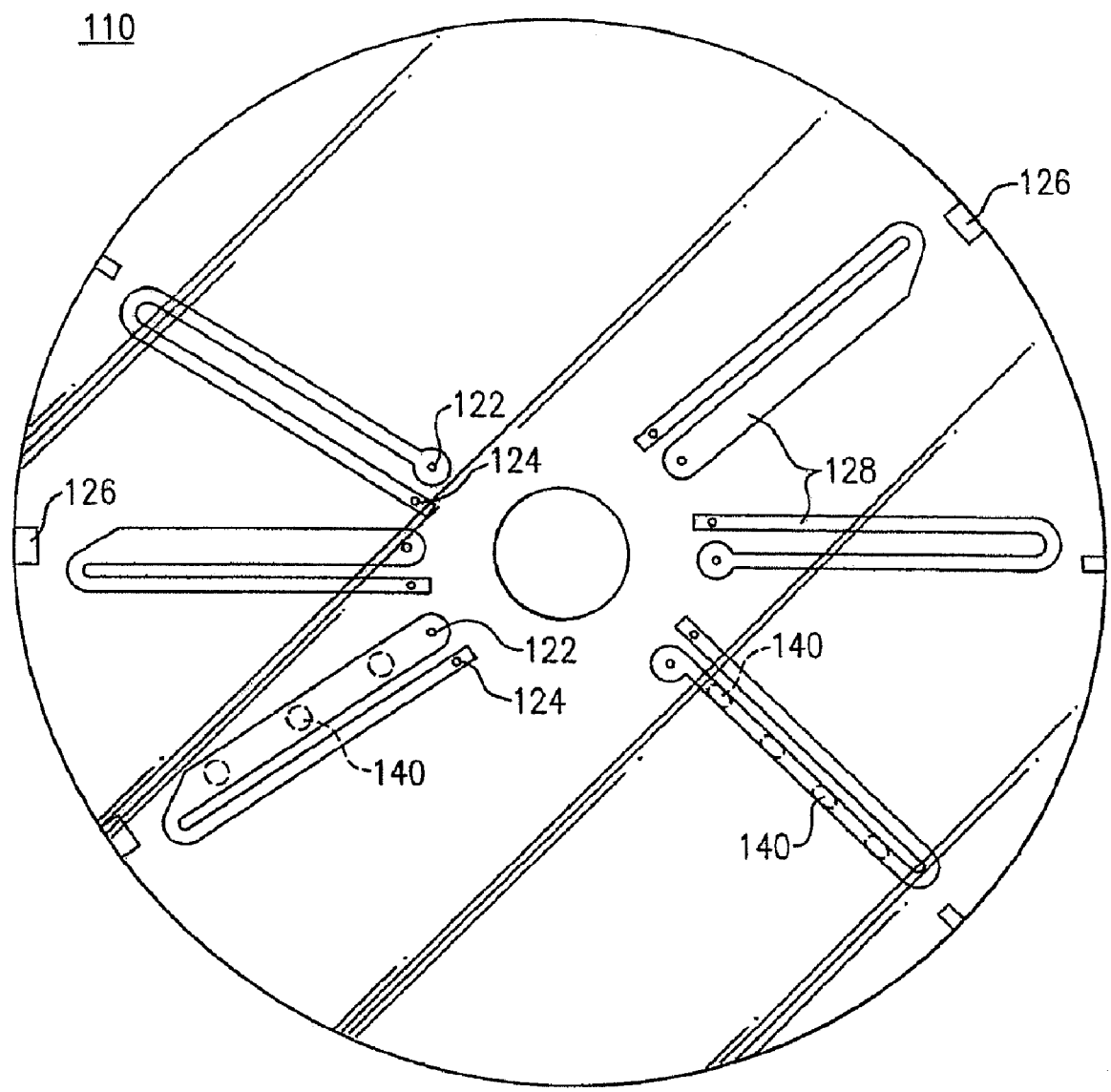
FIG. 8 is a top plan view of the disc shown in FIG. 5.

With reference next to FIG. 8, there is shown a top plan view of the transmissive type optical bio-disc 110 illustrated in FIGS. 5 and 6 with the transparent cap portion 116 revealing the fluidic channels, the trigger markings 126, and the target zones 140 as situated within the disc.

FIG. 9 is an enlarged perspective view of the optical bio-disc 110 according to the transmissive disc embodiment. The disc 110 is illustrated with a portions of the various layers thereof cut away to show a partial sectional view of each principal layer, substrate, coating, or membrane. FIG. 9 illustrates a transmissive disc format with the clear cap portion 116, the thin semi-reflective layer 143 on the substrate 120, and trigger markings 126. In this embodiment, trigger markings 126 include opaque material placed on the top portion of the cap. Alternatively the trigger marking 126 may be formed by clear, non-reflective windows etched on the thin reflective layer 143 of the disc, or any mark that absorbs or does not reflect the signal coming from a trigger detector 160, FIG. 10. FIG. 9 also shows the target zones 140 formed by marking the designated area in the indicated shape or alternatively in any desired shape. Markings to indicate target zone 140 may be made on the thin semi-reflective layer 143 on the substrate 120 or on the bottom portion of the substrate 120 (under the disc). Alternatively, the target zones 140 may be formed by a masking technique that includes masking the entire thin semi-reflective layer 143 except the target zones 140. In this embodiment, target zones 140 may be created by silk screening ink onto the thin semi-reflective layer 143. In the transmissive disc format illustrated in FIGS. 5, 8, and 9, the target zones 140 may alternatively be defined by address information encoded on the disc. In this embodiment, target zones 140 do not include a physically discernable edge boundary.

With continuing reference to FIG. 9, an active layer 144 is illustrated as applied over the thin semi-reflective layer 143. In the preferred embodiment, the active layer 144 is a 10 to 200 µm thick layer of 2% polystyrene. Alternatively, polycarbonate, gold, activated glass, modified glass, or modified polystyrene, for example, polystyrene-co-maleic anhydride, may be used. In addition, hydrogels can be used. As illustrated in this embodiment, the plastic adhesive member 118 is applied over the active layer 144. The exposed section of the plastic adhesive member 118 illustrates the cut out or stamped U-shaped form that creates the fluidic circuits 128.

The final principal structural layer in this transmissive embodiment of the present bio-disc 110 is the clear, non-reflective cap portion 116 that includes inlet ports 122 and vent ports 124.

Referring now to FIG. 10, there is a representation in perspective and block diagram illustrating optical components 148, a light source 150 that produces the incident or interrogation beam 152, a return beam 154, and a transmitted beam 156. In the case of the reflective bio-disc illustrated in FIG. 4, the return beam 154 is reflected from the reflective surface 146 of the cap portion 116 of the optical bio-disc 110. In this reflective embodiment of the present optical bio-disc 110, the return beam 154 is detected and analyzed for the presence of signal elements by a bottom detector 157. In the transmissive bio-disc format, on the other hand, the transmitted beam 156 is detected, by the aforementioned top detector 158, and is also analyzed for the presence of signal elements. In the transmissive embodiment, a photo detector may be used as top detector 158.

FIG. 10 also shows a hardware trigger mechanism that includes the trigger markings 126 on the disc and the aforementioned trigger detector 160. The hardware triggering mechanism is used in both reflective bio-discs (FIG. 4) and transmissive bio-discs (FIG. 9). The triggering mechanism allows the processor 166 to collect data only when the interrogation beam 152 is on a respective target zone 140, e.g. at a predetermined reaction site. Furthermore, in the transmissive bio-disc system, a software trigger may also be used. The software trigger uses the bottom detector to signal the processor 166 to collect data as soon as the interrogation beam 152 hits the edge of a respective target zone 140. FIG. 10 further illustrates a drive motor 162 and a controller 164 for controlling the rotation of the optical bio-disc 110. FIG. 10 also shows the processor 166 and analyzer 168 implemented in the alternative for processing the return beam 154 and transmitted beam 156 associated with the transmissive optical bio-disc.

Figure 11:
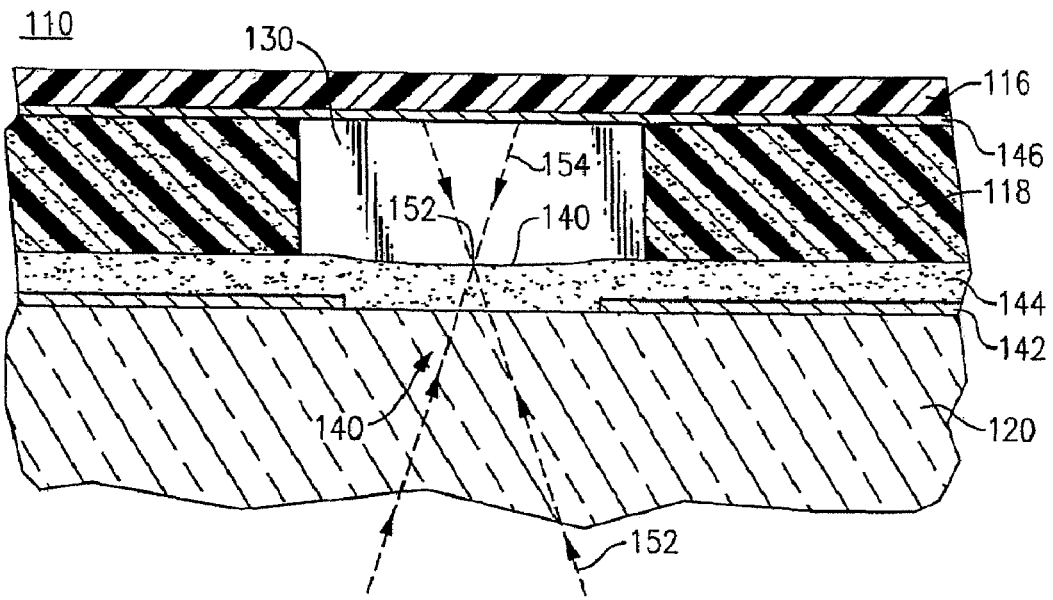
FIG. 11 is a partial cross sectional view taken perpendicular to a radius of the reflective optical bio-disc illustrated in FIGS. 2, 3, and 4 showing a flow channel formed therein.

As shown in FIG. 11, there is presented a partial cross sectional view of the reflective disc embodiment of the optical bio-disc 110. FIG. 11 illustrates the substrate 120 and the reflective layer 142. As indicated above, the reflective layer 142 may be made from a material such as aluminum, gold or other suitable reflective material. In this embodiment, the top surface of the substrate 120 is smooth. FIG. 11 also shows the active layer 144 applied over the reflective layer 142. As also shown in FIG. 11, the target zone 140 is formed by removing an area or portion of the reflective layer 142 at a desired location or, alternatively, by masking the desired area prior to applying the reflective layer 142. As further illustrated in FIG. 11, the plastic adhesive member 118 is applied over the active layer 144. FIG. 11 also shows the cap portion 116 and the reflective surface 146 associated therewith. Thus when the cap portion 116 is applied to the plastic adhesive member 118 including the desired cutout shapes, flow channel 130 is thereby formed. As indicated by the arrowheads shown in FIG. 11, the path of the incident beam 152 is initially directed toward the substrate 120 from below the disc 110. The incident beam then focuses at a point proximate the reflective layer 142. Since this focusing takes place in the target zone 140 where a portion of the reflective layer 142 is absent, the incident continues along a path through the active layer 144 and into the flow channel 130. The incident beam 152 then continues upwardly traversing through the flow channel to eventually fall incident onto the reflective surface 146. At this point, the incident beam 152 is returned or reflected back along the incident path and thereby forms the return beam 154.

FIG. 12 is a partial cross sectional view of the transmissive embodiment of the bio-disc 110. FIG. 12 illustrates a transmissive disc format with the clear cap portion 116 and the thin semi-reflective layer 143 on the substrate 120. FIG. 12 also shows the active layer 144 applied over the thin semi-reflective layer 143. In the preferred embodiment, the transmissive disc has the thin semi-reflective layer 143 made from a metal such as aluminum or gold approximately 100-300 Angstroms thick and does not exceed 400 Angstroms. This thin semi-reflective layer 143 allows a portion of the incident or interrogation beam 152, from the light source 150, FIG. 10, to penetrate and pass upwardly through the disc to be detected by top detector 158, while some of the light is reflected back along the same path as the incident beam but in the opposite direction. In this arrangement, the return or reflected beam 154 is reflected from the semi-reflective layer 143. Thus in this manner, the return beam 154 does not enter into the flow channel 130. The reflected light or return beam 154 may be used for tracking the incident beam 152 on pre-recorded information tracks formed in or on the semi-reflective layer 143 as described in more detail in conjunction with FIGS. 13 and 14. In the disc embodiment illustrated in FIG. 12, a physically defined target zone 140 may or may not be present. Target zone 140 may be created by direct markings made on the thin semi-reflective layer 143 on the substrate 120. These marking may be formed using silk screening or any equivalent method. In the alternative embodiment where no physical indicia are employed to define a target zone (such as, for example, when encoded software addressing is utilized) the flow channel 130 in effect may be employed as a confined target area in which inspection of an investigational feature is conducted.

Figure 13:
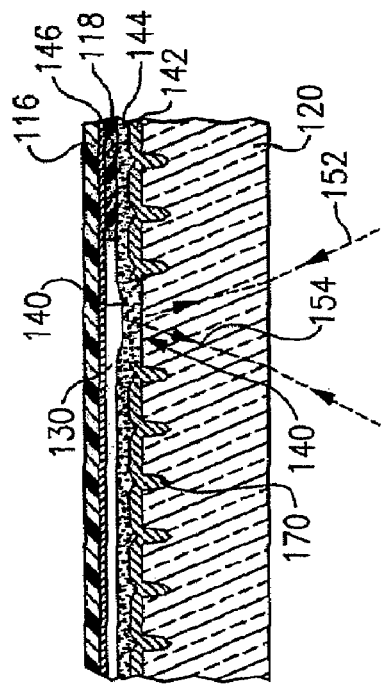
FIG. 13 is a partial longitudinal cross sectional view of the reflective optical bio-disc shown in FIGS. 2, 3, and 4 illustrating a wobble groove formed therein.

FIG. 13 is a cross sectional view taken across the tracks of the reflective disc embodiment of the bio-disc 110. This view is taken longitudinally along a radius and flow channel of the disc. FIG. 13 includes the substrate 120 and the reflective layer 142. In this embodiment, the substrate 120 includes a series of grooves 170. The grooves 170 are in the form of a spiral extending from near the center of the disc toward the outer edge. The grooves 170 are implemented so that the interrogation beam 152 may track along the spiral grooves 170 on the disc. This type of groove 170 is known as a "wobble groove". A bottom portion having undulating or wavy sidewalls forms the groove 170, while a raised or elevated portion separates adjacent grooves 170 in the spiral. The reflective layer 142 applied over the grooves 170 in this embodiment is, as illustrated, conformal in nature. FIG. 13 also shows the active layer 144 applied over the reflective layer 142. As shown in FIG. 13, the target zone 140 is formed by removing an area or portion of the reflective layer 142 at a desired location or, alternatively, by masking the desired area prior to applying the reflective layer 142. As further illustrated in FIG. 13, the plastic adhesive member 118 is applied over the active layer 144. FIG. 13 also shows the cap portion 116 and the reflective surface 146 associated therewith. Thus, when the cap portion 116 is applied to the plastic adhesive member 118 including the desired cutout shapes, the flow channel 130 is thereby formed.

Figure 14:
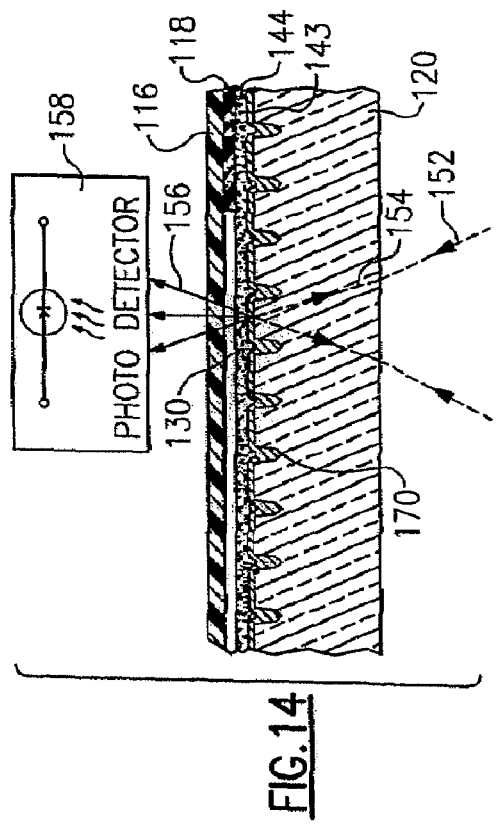
FIG. 14 is a partial longitudinal cross sectional view of the transmissive optical bio-disc illustrated in FIGS. 5, 8, and 9 showing a wobble groove formed therein and a top detector.

FIG. 14 is a cross sectional view taken across the tracks of the transmissive disc embodiment of the bio-disc 110 as described in FIG. 12, for example. This view is taken longitudinally along a radius and flow channel of the disc. FIG. 14 illustrates the substrate 120 and the thin semi-reflective layer 143. This thin semi-reflective layer 143 allows the incident or interrogation beam 152, from the light source 150, to penetrate and pass through the disc to be detected by the top detector 158, while some of the light is reflected back in the form of the return beam 154. The thickness of the thin semi-reflective layer 143 is determined by the minimum amount of reflected light required by the disc reader to maintain its tracking ability. The substrate 120 in this embodiment, like that discussed in FIG. 13, includes the series of grooves 170. The grooves 170 in this embodiment are also preferably in the form of a spiral extending from near the center of the disc toward the outer edge. The grooves 170 are implemented so that the interrogation beam 152 may track along the spiral. FIG. 14 also shows the active layer 144 applied over the thin semi-reflective layer 143. As further illustrated in FIG. 14, the plastic adhesive member or channel layer 118 is applied over the active layer 144. FIG. 14 also shows the cap portion 116 without a reflective surface 146. Thus, when the cap is applied to the plastic adhesive member 118 including the desired cutout shapes, the flow channel 130 is thereby formed and a part of the incident beam 152 is allowed to pass therethrough substantially unreflected.

Figure 16:
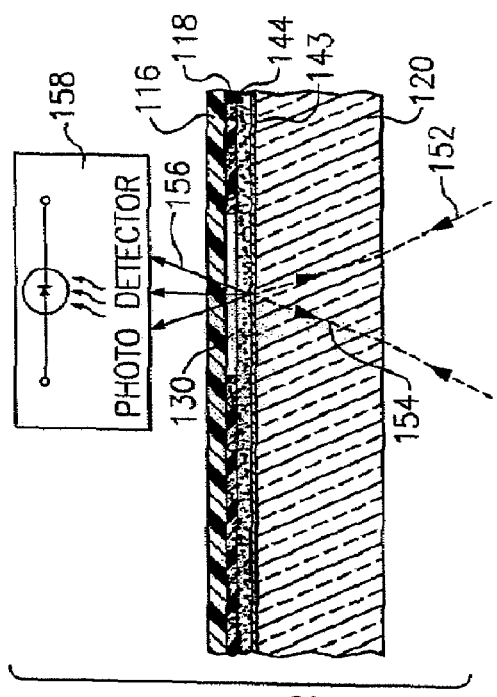
FIG. 16 is a view similar to FIG. 12 showing the entire thickness of the transmissive disc and the initial refractive property thereof.
Figure 15:
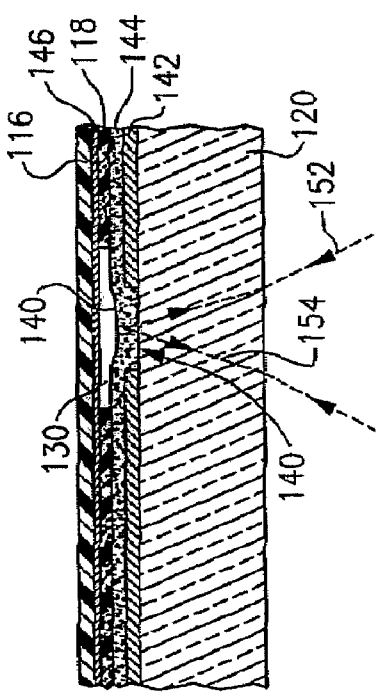
FIG. 15 is a view similar to FIG. 11 showing the entire thickness of the reflective disc and the initial refractive property thereof.

FIG. 15 is a view similar to FIG. 11 showing the entire thickness of the reflective disc and the initial refractive property thereof. FIG. 16 is a view similar to FIG. 12 showing the entire thickness of the transmissive disc and the initial refractive property thereof. Grooves 170 are not seen in FIGS. 15 and 16 since the sections are cut along the grooves 170. FIGS. 15 and 16 show the presence of the narrow flow channel 130 that is situated perpendicular to the grooves 170 in these embodiments. FIGS. 13, 14, 15, and 16 show the entire thickness of the respective reflective and transmissive discs. In these figures, the incident beam 152 is illustrated initially interacting with the substrate 120 which has refractive properties that change the path of the incident beam as illustrated to provide focusing of the beam 152 on the reflective layer 142 or the thin semi-reflective layer 143.

Counting Methods and Related Software

By way of illustrative background, a number of methods and related algorithms for white blood cell counting using optical disc data are herein discussed in further detail. These methods and related algorithms are not limited to counting white blood cells, but may be readily applied to conducting counts of any type of particulate matter including, but not limited to, red blood cells, white blood cells, beads, and any other objects, both biological and non-biological, that produce similar optical signatures that can be detected by an optical reader.

For the purposes of illustration, the following description of the methods and algorithms related to the present invention as described with reference to FIGS. 17-21, are directed to cell counting. With some modifications, these methods and algorithms can be applied to counting other types of objects similar in size to cells. The data evaluation aspects of the cell counting methods and algorithms are described generally herein to provide related background for the methods and apparatus of the present invention. Methods and algorithms for capturing and processing investigational data from the optical bio-disc has general broad applicability and has been disclosed in further detail in commonly assigned U.S. Provisional Application No. 60/291,233 entitled "Variable Sampling Control For Rendering Pixelation of Analysis Results In Optical Bio-Disc Assembly And Apparatus Relating Thereto" filed May 16, 2001 which is herein incorporated by reference and the above incorporated U.S. Provisional Application No. 60/404,921 entitled "Methods For Differential Cell Counts Including Related Apparatus And Software For Performing Same". In the following discussion, the basic scheme of the methods and algorithms with a brief explanation is presented. As illustrated in FIG. 10, information concerning attributes of the biological test sample is retrieved from the optical bio-disc 110 in the form of a beam of electromagnetic radiation that has been modified or modulated by interaction with the test sample. In the case of the reflective optical bio-disc discussed in conjunction with FIGS. 2, 3, 4, 11, 13, and 15, the return beam 154 carries the information about the biological sample. As discussed above, such information about the biological sample is contained in the return beam essentially only when the incident beam is within the flow channel 130 or target zones 140 and thus in contact with the sample. In the reflective embodiment of the bio-disc 110, the return beam 154 may also carry information encoded in or on the reflective layer 142 or otherwise encoded in the wobble grooves 170 illustrated in FIGS. 13 and 14. As would be apparent to one of skill in the art, pre-recorded information is contained in the return beam 154 of the reflective disc with target zones, only when the corresponding incident beam is in contact with the reflective layer 142. Such information is not contained in the return beam 154 when the incident beam 152 is in an area where the information bearing reflective layer 142 has been removed or is otherwise absent. In the case of the transmissive optical bio-disc discussed in conjunction with FIGS. 5, 6, 8, 9, 12, 14, and 16, the transmitted beam 156 carries the information about the biological sample.

With continuing reference to FIG. 10, the information about the biological test sample, whether it is obtained from the return beam 154 of the reflective disc or the transmitted beam 156 of the transmissive disc, is directed to processor 166 for signal processing. This processing involves transformation of the analog signal detected by the bottom detector 157 (reflective disc) or the top detector 158 (transmissive disc) to a discrete digital form.

Figure 17:
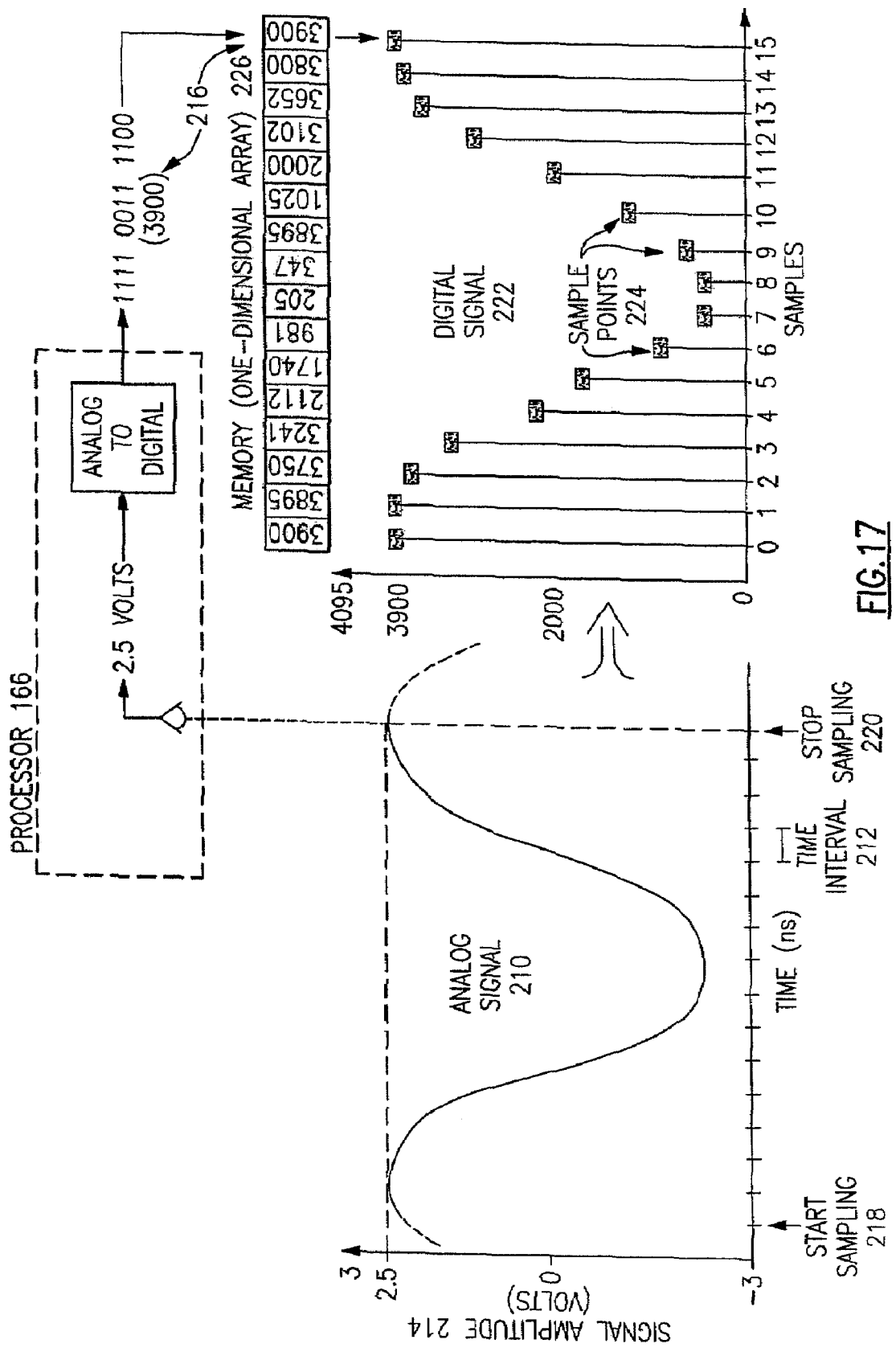
FIG. 17 is a pictorial graphical representation of the transformation of a sampled analog signal to a corresponding digital signal that is stored as a one-dimensional array.

Referring next to FIG. 17, the signal transformation involves sampling the analog signal 210 at fixed time intervals 212, and encoding the corresponding instantaneous analog amplitude 214 of the signal as a discrete binary integer 216. Sampling is started at some start time 218 and stopped at some end time 220. The two common values associated with any analog-to-digital conversion process are sampling frequency and bit depth. The sampling frequency, also called the sampling rate, is the number of samples taken per unit time. A higher sampling frequency yields a smaller time interval 212 between consecutive samples, which results in a higher fidelity of the digital signal 222 compared to the original analog signal 210. Bit depth is the number of bits used in each sample point to encode the sampled amplitude 214 of the analog signal 210. The greater the bit depth, the better the binary integer 216 will approximate the original analog amplitude 214. In the present embodiment, the sampling rate is 8 MHz with a bit depth of 12 bits per sample, allowing an integer sample range of 0 to 4095 (0 to (2n−1), where n is the bit depth. This combination may change to accommodate the particular accuracy necessary in other embodiments. By way of example and not limitation, it may be desirable to increase sampling frequency in embodiments involving methods for counting beads, which are generally smaller than cells. The sampled data is then sent to processor 166 for analog-to-digital transformation.

During the analog-to-digital transformation, each consecutive sample point 224 along the laser path is stored consecutively on disc or in memory as a one-dimensional array 226. Each consecutive track contributes an independent one-dimensional array, which yields a two-dimensional array 228 (FIG. 20A) that is analogous to an image.

Figure 18:
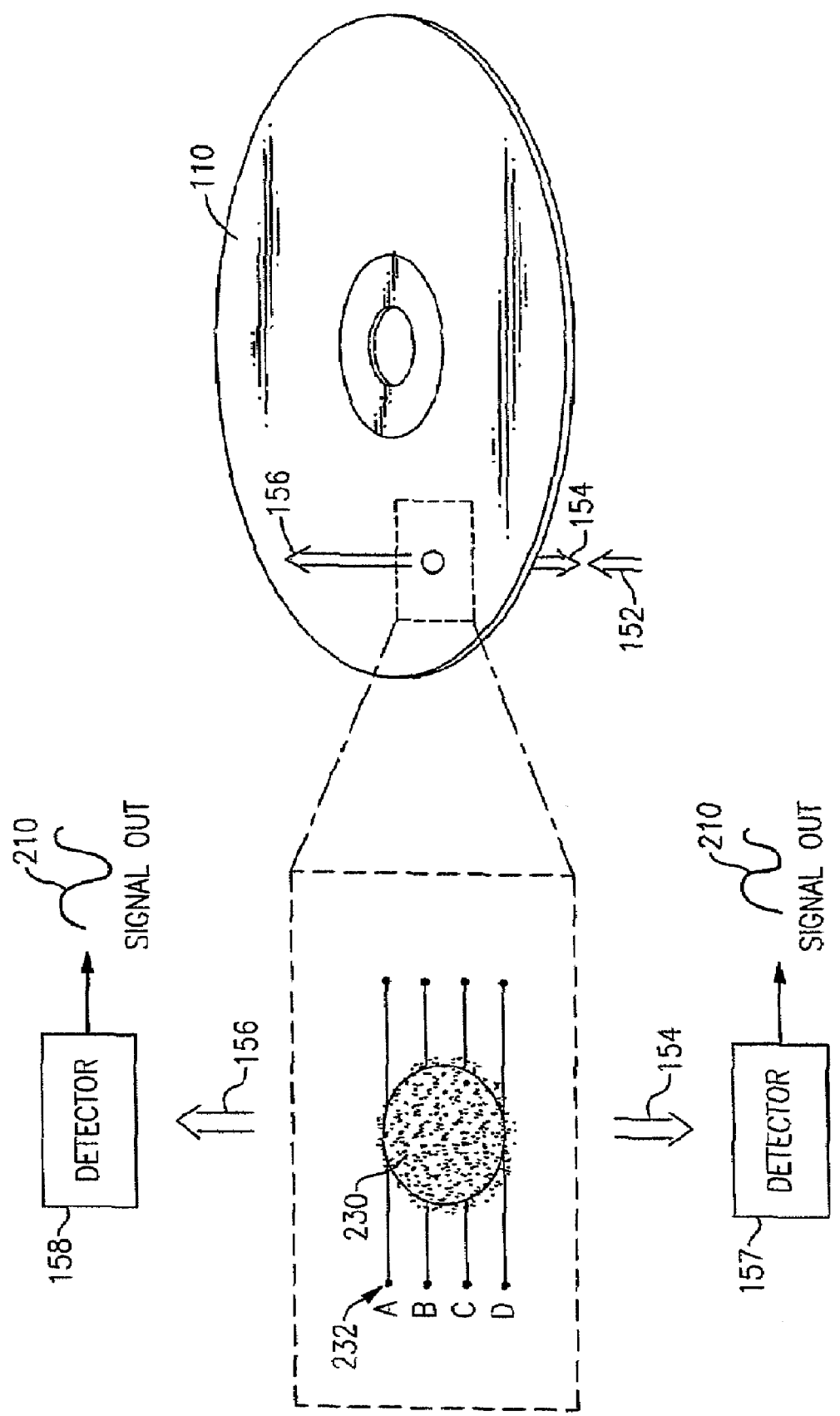
FIG. 18 is a perspective view of an optical disc with an enlarged detailed view of an indicated section showing a captured white blood cell positioned relative to the tracks of the bio-disc yielding a signal-containing beam after interacting with an incident beam.

FIG. 18 is a perspective view of an optical bio-disc 110 with an enlarged detailed perspective view of the section indicated showing a captured white blood cell 230 positioned relative to the tracks 232 of the optical bio-disc. The white blood cell 230 is used herein for illustrative purposes only. As indicated above, other objects or investigational features such as beads or agglutinated matter may be utilized herewith. As shown, the interaction of incident beam 152 with white blood cell 230 yields a signal-containing beam, either in the form of a return beam 154 of the reflective disc or a transmitted beam 156 of the transmissive disc, which is detected by either of detectors 157 or 158.

Figure 19A:
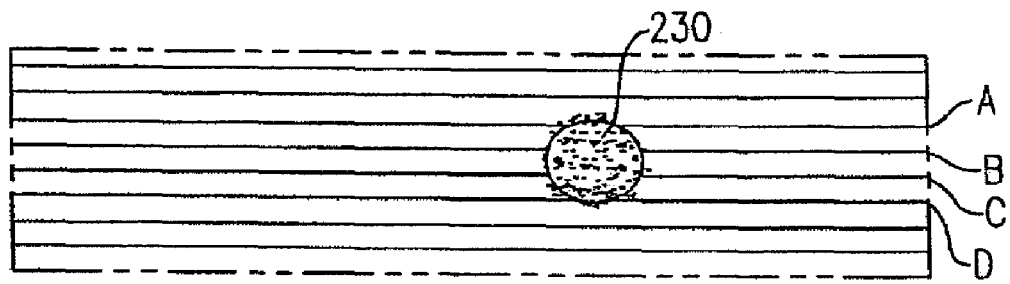
FIG. 19A is a graphical representation of a white blood cell positioned relative to the tracks of an optical bio-disc.
Figure 19B:
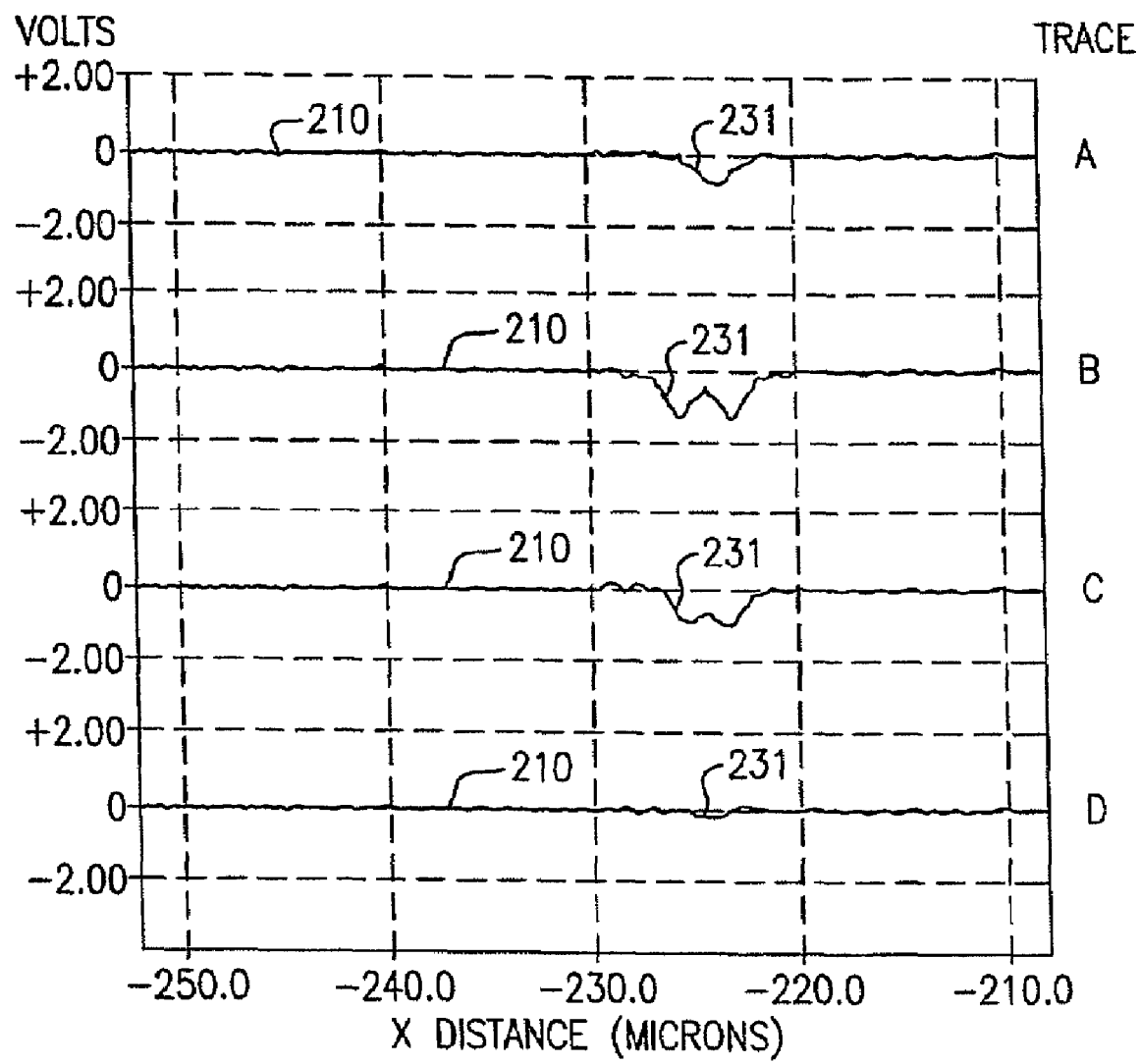
FIG. 19B is a series of signature traces derived from the white blood cell of FIG. 19A.

FIG. 19A is another graphical representation of the white blood cell 230 positioned relative to the tracks 232 of the optical bio-disc 110 shown in FIG. 18. As shown in FIGS. 18 and 19A, the white blood cell 230 covers approximately four tracks A, B, C, and D. FIG. 19B shows a series of signature traces derived from the white blood cell 210 of FIGS. 19 and 19A. As indicated in FIG. 19B, the detection system provides four analogue signals A, B, C, and D corresponding to tracks A, B, C, and D. As further shown in FIG. 19B, each of the analogue signals A, B, C, and D carries specific information about the white blood cell 230. Thus as illustrated, a scan over a white blood cell 230 yields distinct perturbations of the incident beam that can be detected and processed. The analog signature traces (signals) 210 are then directed to processor 166 for transformation to an analogous digital signal 222 as shown in FIGS. 20A and 20C as discussed in further detail below.

Figure 20A:
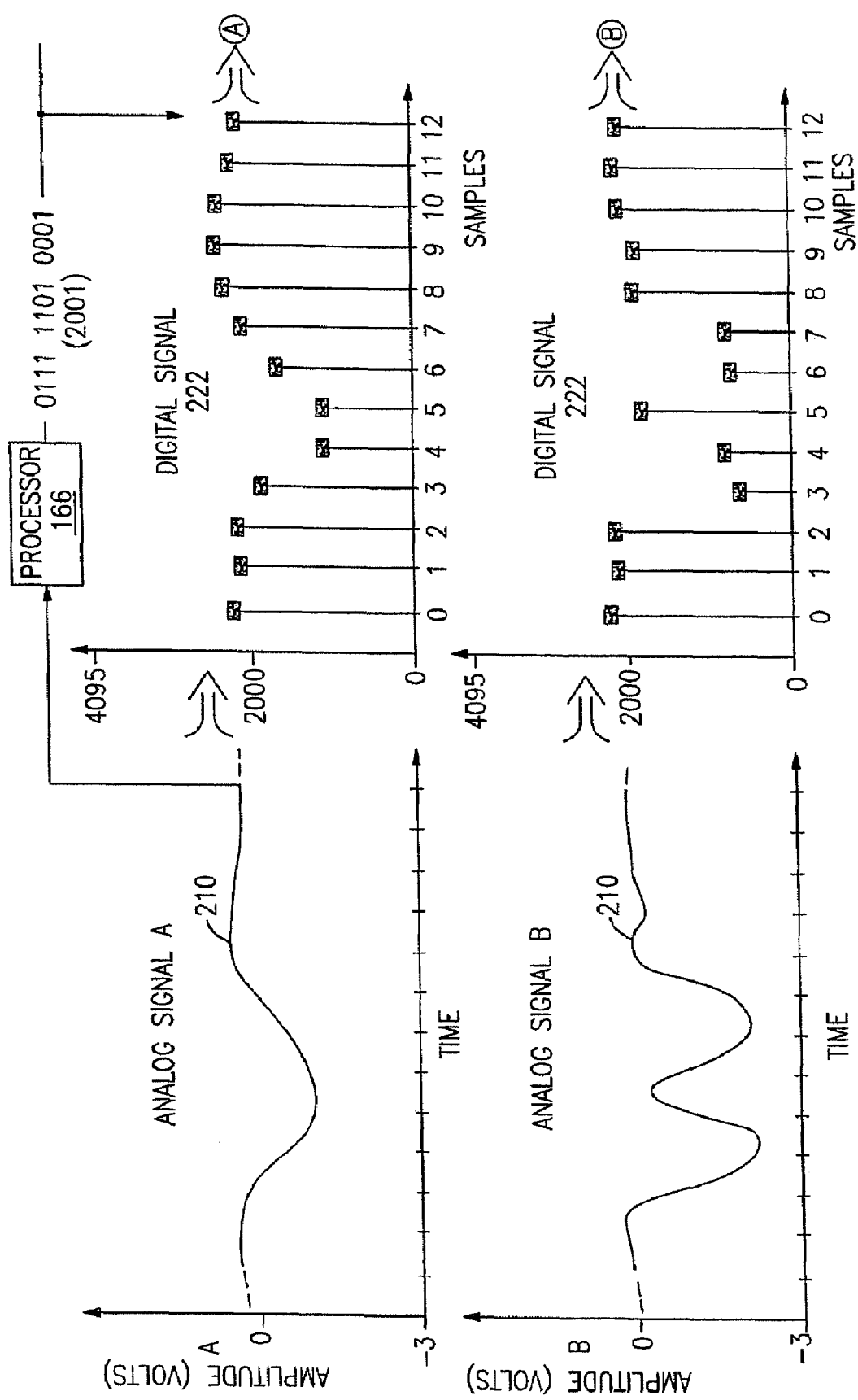
Figure 20B:
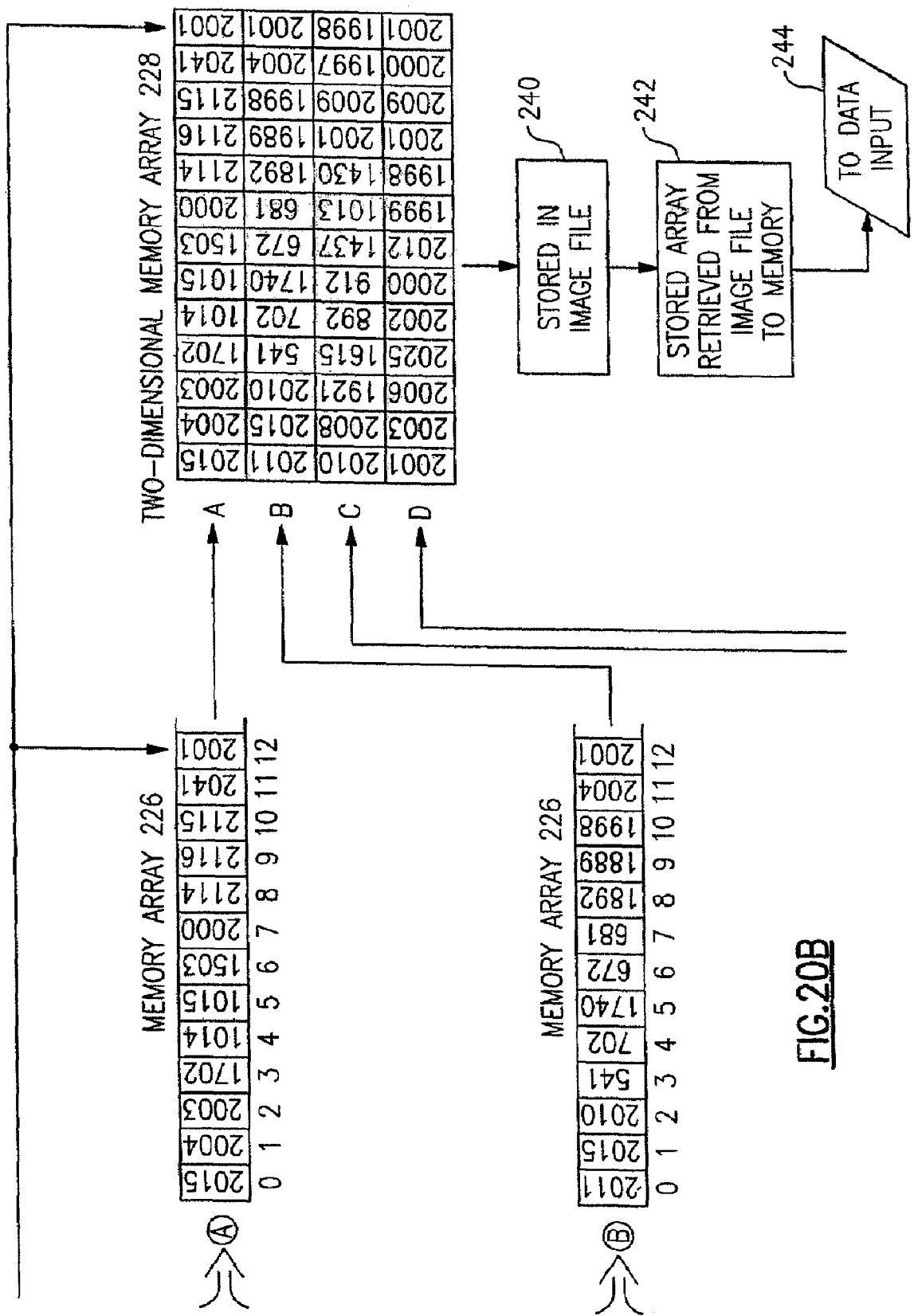
Figure 20C:
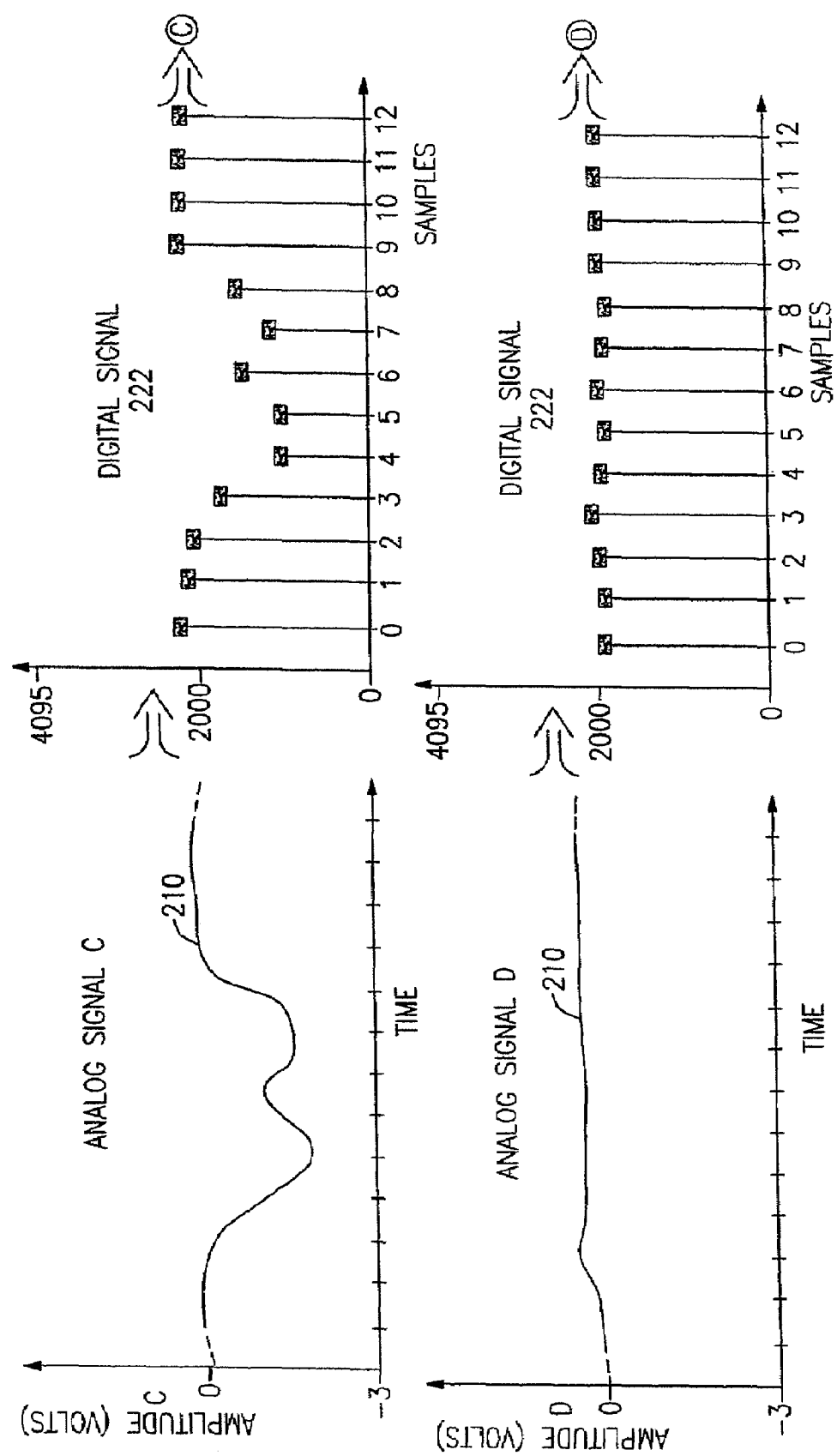

FIG. 20 is a graphical representation illustrating the relationship between FIGS. 20A, 20B, 20C, and 20D. FIGS. 20A, 20B, 20C, and 20D are pictorial graphical representations of transformation of the signature traces from FIG. 19B into digital signals 222 that are stored as one-dimensional arrays 226 and combined into a two-dimensional array 228 for data input 244.

With particular reference now to FIG. 20A, there is shown sampled analog signals 210 from tracks A and B of the optical bio-disc shown in FIGS. 18 and 19A. Processor 166 then encodes the corresponding instantaneous analog amplitude 214 of the analog signal 210 as a discrete binary integer 216 (see FIG. 17). The resulting series of data points is the digital signal 222 that is analogous to the sampled analog signal 210.

Referring next to FIG. 20B, digital signal 222 from tracks A and B (FIG. 20A) is stored as an independent one-dimensional memory array 226. Each consecutive track contributes a corresponding one-dimensional array, which when combined with the previous one-dimensional arrays, yields a two-dimensional array 228 that is analogous to an image. The digital data is then stored in memory or on disc as a two-dimensional array 228 of sample points 224 (FIG. 17) that represent the relative intensity of the return beam 154 or transmitted beam 156 (FIG. 18) at a particular point in the sample area. The two-dimensional array is then stored in memory or on disc in the form of a raw file or image file 240 as represented in FIG. 20B. The data stored in the image file 240 is then retrieved 242 to memory and used as data input 244 to analyzer 168 shown in FIG. 10.

FIG. 20C shows sampled analog signals 210 from tracks C and D of the optical bio-disc shown in FIGS. 18 and 19A. Processor 166 then encodes the corresponding instantaneous analog amplitude 214 of the analog signal 210 as a discrete binary integer 216 (FIG. 17). The resulting series of data points is the digital signal 222 that is analogous to the sampled analog signal 210.

Referring now to FIG. 20D, digital signal 222 from tracks C and D is stored as an independent one-dimensional memory array 226. Each consecutive track contributes a corresponding one-dimensional array, which when combined with the previous one-dimensional arrays, yields a two-dimensional array 228 that is analogous to an image. As above, the digital data is then stored in memory or on disc as a two-dimensional array 228 of sample points 224 (FIG. 17) that represent the relative intensity of the return beam 154 or transmitted beam 156 (FIG. 18) at a particular point in the sample area. The two-dimensional array is then stored in memory or on disc in the form of a raw file or image file 240 as shown in FIG. 20B.

As indicated above, the data stored in the image file 240 is then retrieved 242 to memory and used as data input 244 to analyzer 168 FIG. 10.

The computational and processing algorithms are stored in analyzer 168 (FIG. 10) and applied to the input data 244 to produce useful output results 262 (FIG. 21) that may be displayed on the display monitor 114 (FIG. 10).

Figure 21:
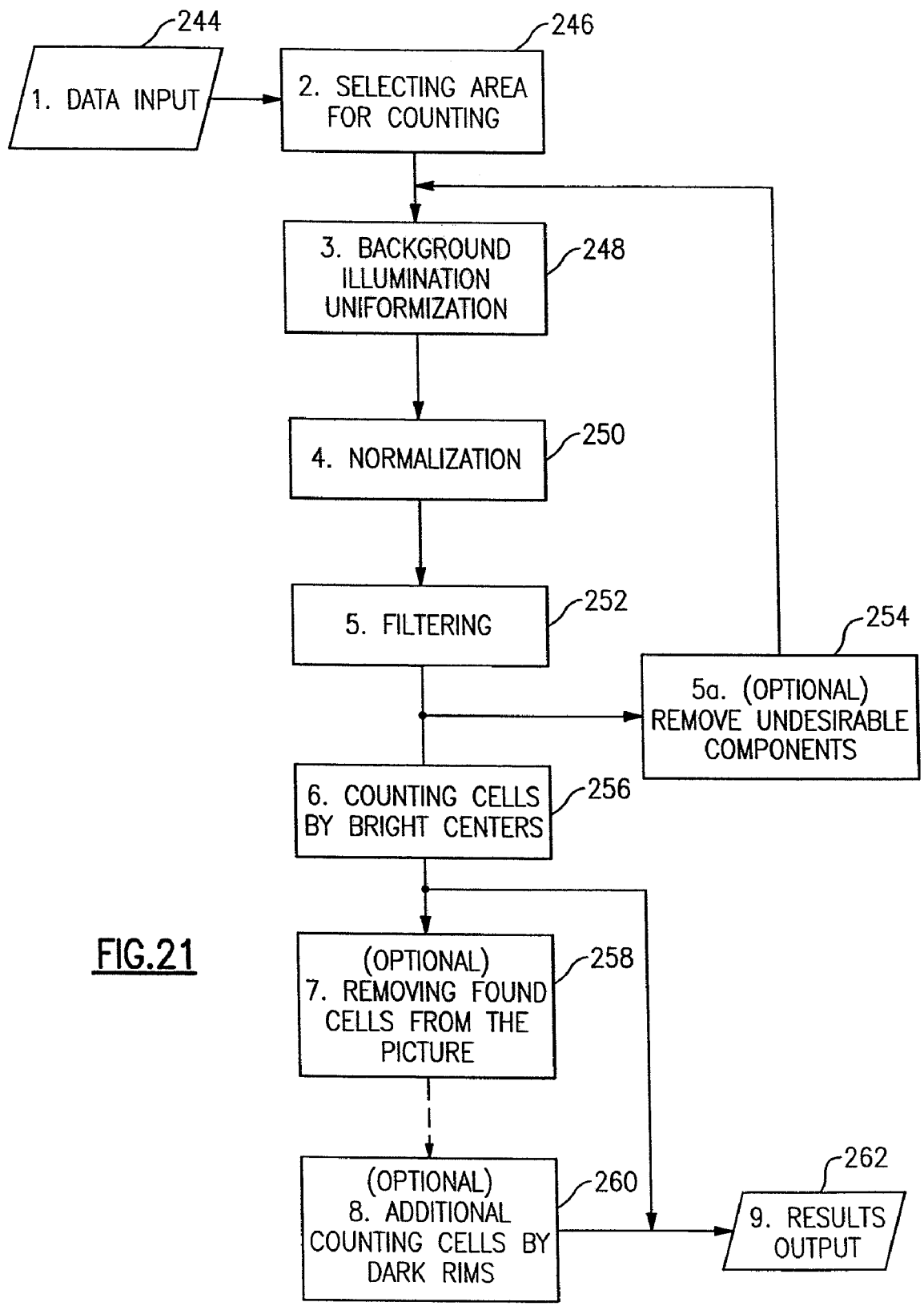
FIG. 21 is a logic flow chart depicting the principal steps for data evaluation according to processing methods and computational algorithms related to the present invention.

With reference now to FIG. 21 there is shown a logic flow chart of the principal steps for data evaluation according to the processing methods and computational algorithms related to the present invention. A first principal step of the present processing method involves receipt of the input data 244. As described above, data evaluation starts with an array of integers in the range of 0 to 4096.

The next principle step 246 is selecting an area of the disc for counting. Once this area is defined, an objective then becomes making an actual count of all white blood cells contained in the defined area. The implementation of step 246 depends on the configuration of the disc and users options. By way of example and not limitation, embodiments of the invention using discs with windows such as the target zones 140 shown in FIGS. 2 and 5, the software recognizes the windows and crops a section thereof for analysis and counting. In one preferred embodiment, such as that illustrated in FIG. 2, the target zones or windows have the shape of 1×2 mm rectangles with a semicircular section on each end thereof. In this embodiment, the software crops a standard rectangle of 1×2 mm area inside a respective window. In an aspect of this embodiment, the reader may take several consecutive sample values to compare the number of cells in several different windows.

In embodiments of the invention using a transmissive disc without windows, as shown in FIGS. 5, 6, 8, and 9, step 246 may be performed in one of two different manners. The position of the standard rectangle is chosen either by positioning its center relative to a point with fixed coordinates, or by finding reference mark which may be a spot of dark dye. In the case where a reference mark is employed, a dye with a desired contrast is deposited in a specific position on the disc with respect to two clusters of cells. The optical disc reader is then directed to skip to the center of one of the clusters of cells and the standard rectangle is then centered around the selected cluster.

As for the user options mentioned above in regard to step 246, the user may specify a desired sample area shape for cell counting, such as a rectangular area, by direct interaction with mouse selection or otherwise. In the present embodiment of the software, this involves using the mouse to click and drag a rectangle over the desired portion of the optical bio-disc-derived image that is displayed on monitor 114. Regardless of the evaluation area selection method, a respective rectangular area is evaluated for counting in the next step 248.

The third principal step in FIG. 21 is step 248, which is directed to background illumination uniformization. This process corrects possible background uniformity fluctuations caused in some hardware configurations. Background illumination uniformization offsets the intensity level of each sample point such that the overall background, or the portion of the image that is not cells, approaches a plane with an arbitrary background value Vbackground. While Vbackground may be decided in many ways, such as taking the average value over the standard rectangular sample area, in the present embodiment, the value is set to 2000. The value V at each point P of the selected rectangular sample area is replaced with the number (Vbackground+(V−average value over the neighborhood of P)) and truncated, if necessary, to fit the actual possible range of values, which is 0 to 4095 in a preferred embodiment of the present invention. The dimensions of the neighborhood are chosen to be sufficiently larger than the size of a cell and sufficiently smaller than the size of the standard rectangle.

The next step in the flow chart of FIG. 21 is a normalization step 250. In conducting normalization step 250, a linear transform is performed with the data in the standard rectangular sample area so that the average becomes 2000 with a standard deviation of 600. If necessary, the values are truncated to fit the range 0 to 4096. This step 250, as well as the background illumination uniformization step 248, makes the software less sensitive to hardware modifications and tuning. By way of example and not limitation, the signal gain in the detection circuitry, such as top detector 158 (FIG. 18), may change without significantly affecting the resultant cell counts.

As shown in FIG. 21, a filtering step 252 is next performed. For each point P in the standard rectangle, the number of points in the neighborhood of P, with dimensions smaller than indicated in step 248, with values sufficiently distinct from Vbackground is calculated. The points calculated should approximate the size of a cell in the image. If this number is large enough, the value at P remains as it was; otherwise it is assigned to Vbackground. This filtering operation is performed to remove noise, and in the optimal case only cells remain in the image while the background is uniformly equal Vbackground.

An optional step 254 directed to removing bad components may be performed as indicated in FIG. 21. Defects such as scratches, bubbles, dirt, and other similar irregularities may pass through filtering step 252. These defects may cause cell counting errors either directly or by affecting the overall distribution in the images histogram. Typically, these defects are sufficiently larger in size than cells and can be removed in step 254 as follows. First a binary image with the same dimensions as the selected region is formed. A in the binary image is defined as white, if the value at the corresponding point of the original image is equal to Vbackground, and black otherwise. Next, connected components of black points are extracted. Then subsequent erosion and expansion are applied to regularize the view of components. And finally, components that are larger than a defined threshold are removed. In one embodiment of this optional step, the component is removed from the original image by assigning the corresponding sample points in the original image with the value Vbackground. The threshold that determines which components constitute countable objects and which are to be removed is a user-defined value. This threshold may also vary depending on the investigational feature being counted i.e. white blood cells, red blood cells, or other biological matter. After optional step 254, steps 248, 250, and 252 are preferably repeated.

The next principal processing step shown in FIG. 21 is step 256, which is directed to counting cells by bright centers. The counting step 256 consists of several substeps. The first of these substeps includes performing a convolution. In this convolution substep, an auxiliary array referred to as a convolved picture is formed. The value of the convolved picture at point P is the result of integration of a picture after filtering in the circular neighborhood of P. More precisely, for one specific embodiment, the function that is integrated, is the function that equals v−2000 when v is greater than 2000 and 0 when v is less than or equal to 2000. The next substep performed in counting step 256 is finding the local maxima of the convolved picture in the neighborhood of a radius about the size of a cell. Next, duplicate local maxima with the same value in a closed neighborhood of each other are avoided. In the last substep in counting step 256, the remaining local maxima are declared to mark cells.

In some hardware configurations, some cells may appear without bright centers. In these instances, only a dark rim is visible and the following two optional steps 258 and 260 are useful.

Step 258 is directed to removing found cells from the picture. In step 258, the circular region around the center of each found cell is filled with the value 2000 so that the cells with both bright centers and dark rims would not be found twice.

Step 260 is directed to counting additional cells by dark rims. Two transforms are made with the image after step 258. In the first substep of this routine, substep (a), the value v at each point is replaced with (2000-v) and if the result is negative it is replaced with zero. In substep (b), the resulting picture is then convolved with a ring of inner radius R1 and outer radius R2. R1 and R2 are, respectively, the minimal and the maximal expected radius of a cell, the ring being shifted, subsequently, in substep (d) to the left, right, up and down. In substep (c), the results of four shifts are summed. After this transform, the image of a dark rim cell looks like a four petal flower. Finally in substep (d), maxima of the function obtained in substep (c) are found in a manner to that employed in counting step 256. They are declared to mark cells omitted in step 256.

After counting step 256, or after counting step 260 when optionally employed, the last principal step illustrated in FIG. 21 is a results output step 262. The number of cells found in the standard rectangle is displayed on the monitor 114 shown in FIGS. 1 and 5, and each cell identified is marked with a cross on the displayed optical bio-disc-derived image.

Additional computer science methodologies and apparatus directed to extracting and visualizing data from bio-discs and/or optical analysis discs are discussed in commonly assigned U.S. patent application Ser. No. 10/341,326 entitled "Method and Apparatus for Visualizing Data" filed Jan. 13, 2003 and U.S. patent application Ser. No. 10/345,122 entitled "Methods and Apparatus for Extracting Data From an Optical Analysis Disc" filed on Jan. 14, 2003 both of which have been herein incorporated by reference.

Triggering Through Disc Grooves

Figure 22:
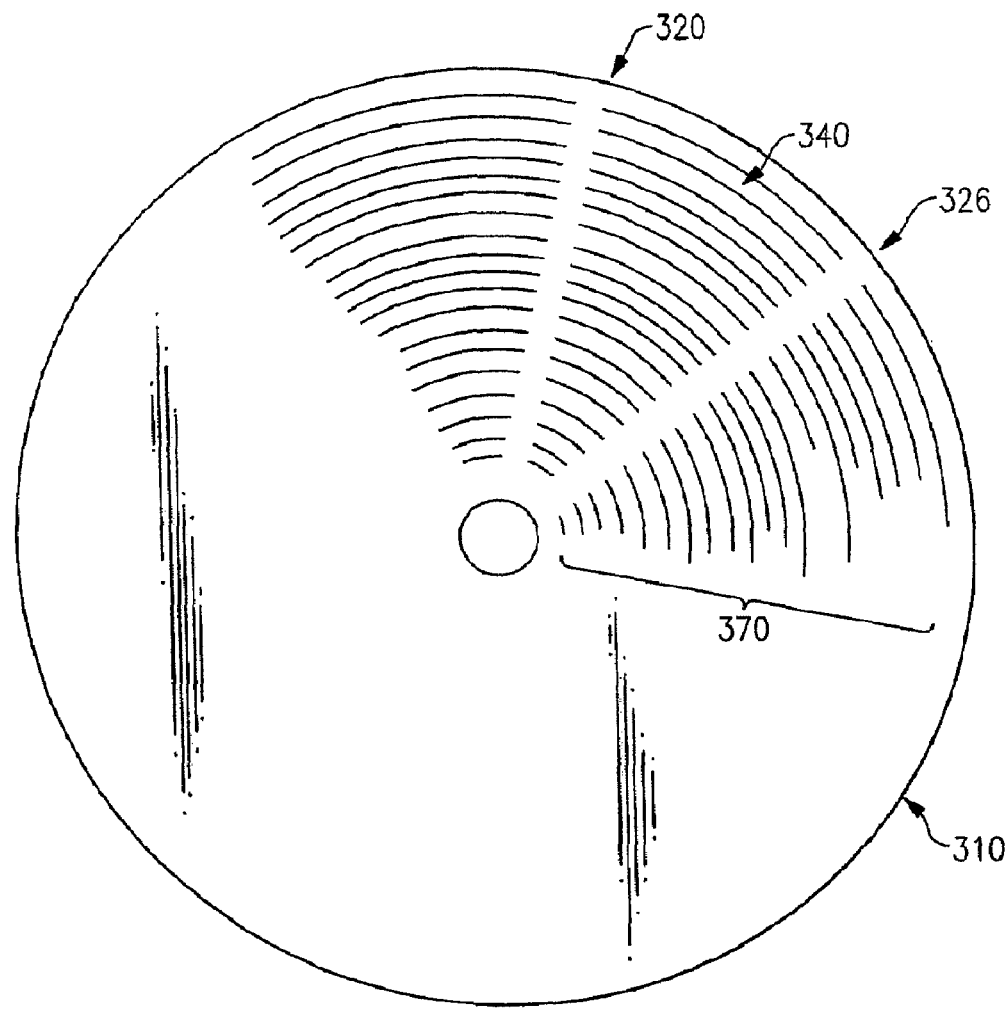
FIG. 22 is a top view of a first embodiment of an optical analysis disc according to the present invention.

Referring now to FIG. 22 a first embodiment of an optical analysis disc 310 according to the present invention is shown.

The disc 310, has a physical structure according to one of the above described embodiments, and includes trigger marks 326. Trigger marks 326, as already described, are used for determining the angular position of the disc during its rotation in order to identify specific target regions 340, where the analysis are to be performed.

According to this embodiment, the disc 310 includes grooves 370 adapted to define corresponding laser-readable tracks on the disc itself.

As shown in FIG. 22, each of such trigger marks 326 defines a respective triggering region provided by a radial interruption of the grooves 370 of the disc. First and second interruptions are provided in order to delimit a particular target region 340.

With reference to manufacturing details as hereto described (FIGS. 4, 11, 13), it can be easily observed that, the reflection levels of the laser beam in correspondence to such interruptions, is that of a 'mirror' or straight reflection coefficient of the reflective layer 146.

Since no unexpected disturbance of the disc can result in increased reflection, this signal is easily and uniquely recognized as arising from the interruption in the grooves. Therefore the reflection increase can be used for generating a trigger signal in order to determine the start of a corresponding target region 340.

According to the present invention, a method for triggering through interrupted grooves of an optical analysis disc is provided. This method includes the steps of detecting interruption in the grooves, generating an electrical reflection signal corresponding to the interruptions detected, and elaborating the reflection signal to thereby generate a trigger signal. In particular, according to the present invention, the detecting phase is performed by directing a laser beam toward the interruption and then detecting a reflected laser beam.

Figure 23:
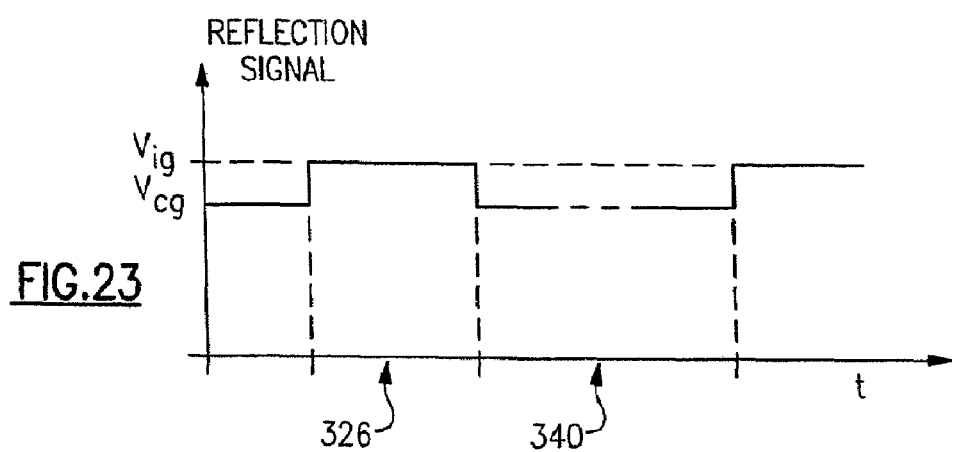
FIG. 23 is a graph representing a reflection signal extracted by the disc of FIG. 22.

An example of such reflection signal is illustrated in the FIG. 23. Because of the reflection features of the disc, the resulting reflection signal has a first intensity value Vcg when the laser beam is reflected by a continuous groove and a second intensity value Vig when the laser beam is reflected by an interruption of the grooves. In particular, the second intensity value Vig is greater than the first intensity value Vcg. Such intensity increase can be advantageously used for determining a trigger signal.

Figure 24:
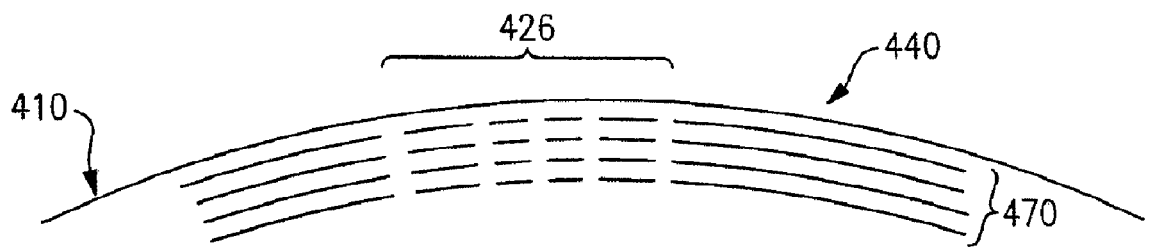
FIG. 24 is a partial top view of a second embodiment of an optical analysis disc according to the present invention.

Referring now to FIG. 24, a partial top view of a second embodiment of an optical analysis disc 410 according to the present invention is shown. The construction details related to the disc will not be here described because they are common to the other embodiments already disclosed. According to such second embodiment the disc 410 has triggering regions 426 defined by one or more interruptions of the grooves 470, such interruptions sequence defining a pattern of interrupted grooves. The pattern encodes information apt to identify a trigger signal that will determine the start of the target region 440.

Figure 25A:
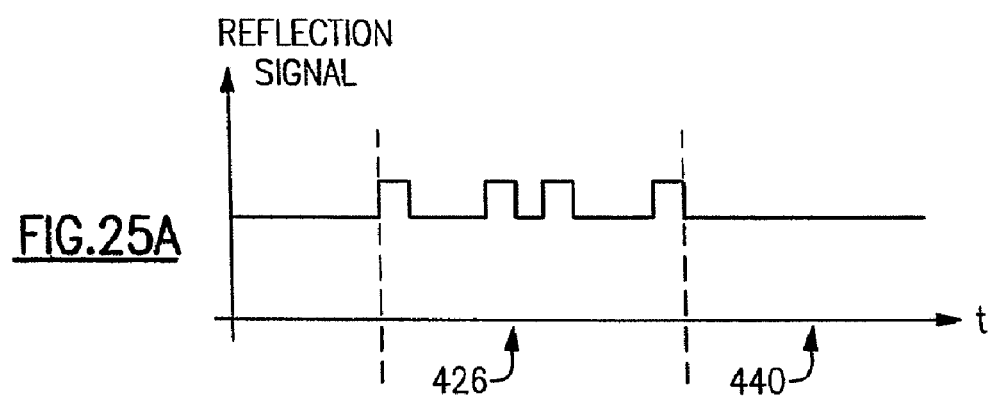
FIG. 25A is a graph representing a reflection signal extracted by the disc of FIG. 24.
Figure 25B:
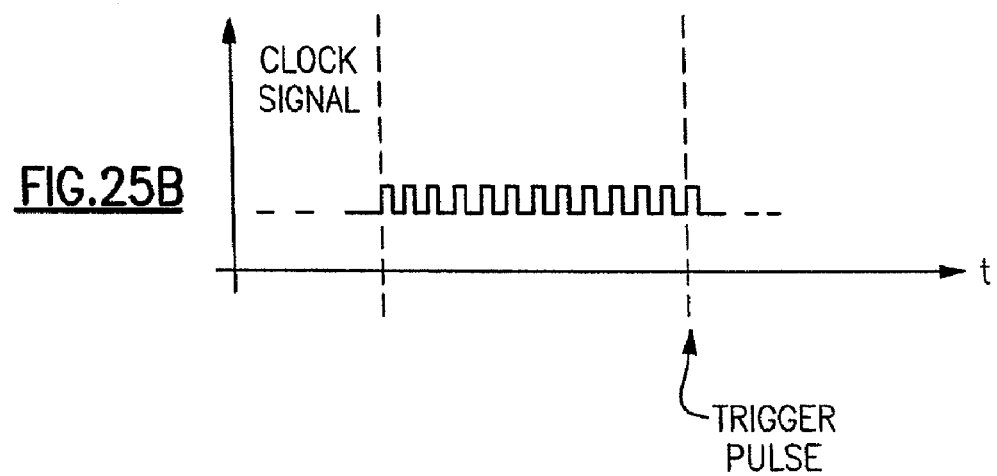
FIG. 25B is a graph of a clock signal generated by the reflection signal of FIG. 25A.

The next FIG. 25A is a graph representing a reflection signal corresponding to the pattern of FIG. 24. According to this second embodiment, the pattern of interrupted grooves is advantageously used to encode data in the signal read out by the reader, i.e. in order to extract a clock signal. The encoded data is used to uniquely identify which particular clock pulse is the trigger mark (FIG. 25B). The advantages of this scheme are that make it possible to use a clock pulse sequence for determining the trigger signal in a more accurately way with respect to a single transition, since it depends upon multiple transitions with the associated noise reduction. Furthermore the trigger timing is much less dependent on the readout accuracy of a single feature on the disc, and is therefore much less sensitive to influences that disturb the readout signal (such as dirt, optical aberration etc) and the physical position of the trigger mark.

Optionally, the data encoding may use standard error correction techniques to improve robustness. The frequency (or spatial size) of the interruptions in the grooves may be optimized for robust readout also, since high data density is not the primary aim. Therefore as long as the clock pulse period is sufficiently short for the required triggering accuracy, the individual features may be longer than the T3 length of standard EFM encoding, i.e. they may be greater than a micron.

Figure 26:
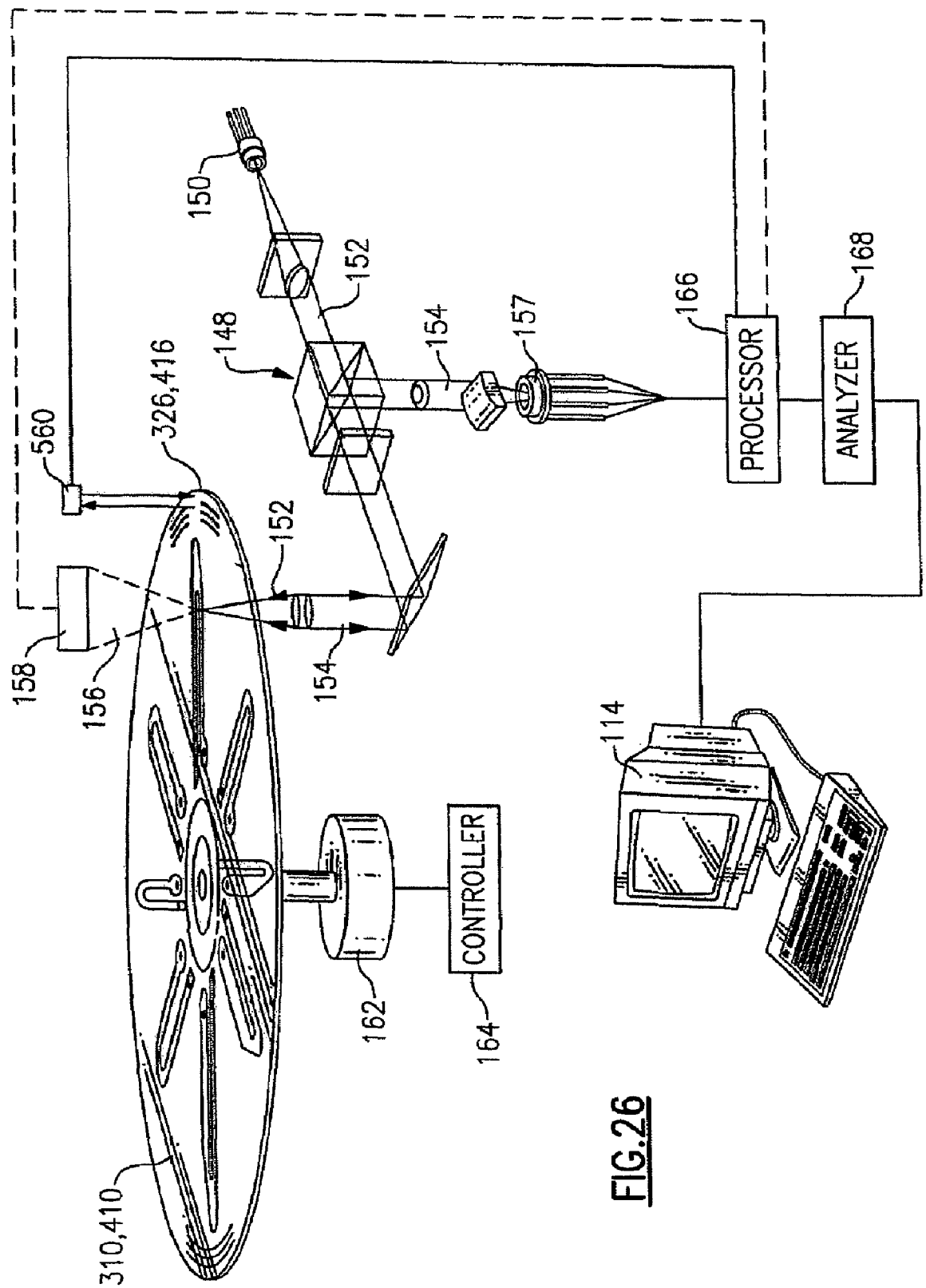
FIG. 26 is a perspective and block diagram representation illustrating an optical analysis disc system according to the present invention.

An optical analysis disc system according to the present invention is schematically illustrated in the next FIG. 26. Such system includes a trigger mechanism including a trigger detector 560 adapted to detect trigger marks 326, 426 provided on an optical analysis disc 310, 410. The trigger detector 560 is adapted to direct a laser beam towards the trigger marks and detect a reflected laser beam. The reflected laser beam is advantageously used for generating a corresponding electrical reflection signal, that can be acquired by a processor 166 having means for elaborating such reflection signal.

In particular such elaborating means may include an apparatus for regenerating a clock signal, starting from the reflection signal, for example a slicer/PLL type apparatus.

A counter device can be advantageously used to count a predetermined number of clock pulses for determining a clock pulse corresponding to a trigger signal.

Furthermore, in order to improve robustness, the encoded data can be optionally treated by such elaborating means, using standard error correction techniques.

CONCLUDING STATEMENTS

All patents, provisional applications, patent applications, and other publications mentioned in this specification are incorporated herein by reference in their entireties.

While this invention has been described in detail with reference to certain preferred embodiments, it should be appreciated that the present invention is not limited to those precise embodiments. Rather, in view of the present optical bio-disclosure that describes the current best mode for practicing the invention, many modifications and variations would present themselves to those of skill in the art without departing from the scope and spirit of this invention. The scope of the invention is, therefore, indicated by the following claims rather than by the foregoing description. All changes, modifications, and variations coming within the meaning and range of equivalency of the claims are to be considered within their scope.

Furthermore, those skilled in the art will recognize, or be able to ascertain, using no more than routine experimentation, many equivalents to the specific embodiments of the invention described herein. Such equivalents are also intended to be encompassed by the following claims.

What is claimed is:

1. An optical bio-disc analysis system for analyzing biological samples positioned on analysis zones of a bio-disc, the analysis system comprising:
    a rotation mechanism configured to support and rotate the bio-disc;
    a detector configured to detect at least a current intensity of an optical signal reflected from the bio-disc;
    a trigger module configured to detect interruptions in one or more grooves of the bio-disc as the bio-disc rotates;
    a processing module configured to determine a current angular position of the bio-disc with reference to the detector based at least partly on the current intensity of the reflected optical signal.

2. The system of claim 1, further comprising a laser module configured to direct a laser beam toward said bio-disc.

3. The system of claim 1, wherein the reflected optical signal has a first intensity value when an optical signal is reflected by one of the grooves and a second intensity value when the optical signal is reflected by an interruption of the grooves.

4. The system of claim 3, wherein the one or more interruptions of the bio-disc comprises reflective characteristics of a mirror.

5. The system of claim 2, wherein detection of one or more of the interruptions indicates that the laser beam is proximate one of the analysis zones.

6. The system of claim 3 wherein the second intensity value is greater than the first intensity value.

7. The system of claim 3, wherein the processing module is further configured to regenerate a clock signal based at least partly on the respective time gaps between circular grooves and interruptions on the bio-disc.

8. The system of claim 3, wherein the processing module is further configured to determine data encoded in the interruptions of the bio-disc.

9. The system of claim 8, wherein the processing module is further configured to perform error correction on the encoded data.

10. The system of claim 1 wherein the processing module comprises a microprocessor.

11. The system of claim 7 wherein the processing module comprises a slicer/PLL type apparatus.

12. The system of claim 7 wherein the processing module comprises a counter device that counts a predetermined number of clock pulses for determining a clock pulse corresponding to a trigger signal.

13. A method of analyzing biological samples positioned on analysis zones of a bio-disc, the method comprising:
    rotating a bio-disc comprising one or more analysis zones, wherein the bio-disc comprises one or more interruptions in a substantially circular groove of the bio-disc proximate each of the one or more analysis zones;
    detecting at least a current intensity of an optical signal reflected from the bio-disc;
    determining a current angular position of the bio-disc based at least partly on the current intensity of the reflected optical signal.

14. The method of claim 13, wherein an increase in the current intensity of the reflected optical signal compared to a previous intensity of the reflected optical signal indicates a position of an analysis zone.

15. The method of claim 13, further comprising initiating analysis of a biological sample in an analysis zone of the bio-disc in response to determining that the current angular position of the bio-disc is such that the biological sample may be analyzed.

16. A system of analyzing biological samples positioned on analysis zones of a bio-disc, the method comprising:
    means for rotating a bio-disc comprising one or more analysis zones, wherein the bio-disc comprises one or more interruptions in a substantially circular groove of the bio-disc proximate each of the one or more analysis zones;
    means for detecting at least a current intensity of an optical signal reflected from the bio-disc;
    means for determining a current angular position of the bio-disc based at least partly on the current intensity of the reflected optical signal.

* * * * *

UNITED STATES PATENT AND TRADEMARK OFFICE
CERTIFICATE OF CORRECTION

| | |
|---|---|
| PATENT NO. | : 7,428,200 B2 |
| APPLICATION NO. | : 11/781104 |
| DATED | : September 23, 2008 |
| INVENTOR(S) | : James Howard Coombs et al. |

It is certified that error appears in the above-identified patent and that said Letters Patent is hereby corrected as shown below:

Page 2, On the Title Pg Item (56)

Line 1, Under Other Publications, change "Repeort" to --Report--.

Figure 4 (Drawings)

Figure 4, Below "118" insert --144--.

Column 3

Line 25, Change "Agglutinates" to --Agglutinants--.

Column 9

Line 23, Change "portions" to --portion--.

Column 15

Line 19, Change "users" to --user's--.

Signed and Sealed this

Seventeenth Day of March, 2009

JOHN DOLL
*Acting Director of the United States Patent and Trademark Office*